(12) United States Patent
Harrison et al.

(10) Patent No.: US 10,400,452 B2
(45) Date of Patent: Sep. 3, 2019

(54) CONSTRUCTION PANELS, MATERIALS, SYSTEMS, AND METHODS

(71) Applicant: Georgia-Pacific Gypsum LLC, Atlanta, GA (US)

(72) Inventors: Charles R. Harrison, Acworth, GA (US); Lawrence Gollob, Stone Mountain, GA (US); Clarence A. Shelton, Atlanta, GA (US); Stuart Brandon Gilley, Atlanta, GA (US); Timothy R. Fierbaugh, Fayetteville, GA (US)

(73) Assignee: Georgia-Pacific Gypsum LLC, Atlanta, GA (US)

( * ) Notice: Subject to any disclaimer, the term of this patent is extended or adjusted under 35 U.S.C. 154(b) by 109 days.

(21) Appl. No.: 16/047,132

(22) Filed: Jul. 27, 2018

(65) Prior Publication Data

US 2018/0371754 A1 Dec. 27, 2018

Related U.S. Application Data

(63) Continuation-in-part of application No. 15/703,322, filed on Sep. 13, 2017, now Pat. No. 10,151,104, (Continued)

(51) Int. Cl.
*E04C 2/26* (2006.01)
*G01N 27/04* (2006.01)
*E04C 2/52* (2006.01)
*G08B 21/20* (2006.01)
*G01N 27/48* (2006.01)

(52) U.S. Cl.
CPC ............... *E04C 2/526* (2013.01); *E04C 2/26* (2013.01); *G01N 27/048* (2013.01); *G08B 21/20* (2013.01)

(58) Field of Classification Search
CPC ............ G01K 1/14; G01N 27/48; E04C 2/26
See application file for complete search history.

(56) References Cited

U.S. PATENT DOCUMENTS 5,319,900 A * 6/1994 Lehnert ............... B28B 19/0092
106/772
6,342,284 B1 6/2002 Yu et al.
(Continued)

FOREIGN PATENT DOCUMENTS

JP 2007-310506 A 11/2007
JP 2007310506 A * 11/2007
WO 2015/184460 A2 12/2015

OTHER PUBLICATIONS

International Search Report and Written Opinion for PCT/US2017/021780, dated May 10, 2017 (27 pages).

*Primary Examiner* — Jamel E Williams
(74) *Attorney, Agent, or Firm* — Eversheds Sutherland (US) LLP; Stacy Fredrich; Sam W. Sabnis

(57) ABSTRACT

Construction panels and other materials, methods for their manufacture, and systems and methods for monitoring environmental conditions with such panels are provided herein. The panels include at least one environmental sensor assembly associated with a panel core and configured to detect an environmental condition of the panel comprising moisture, pressure, or both, and wirelessly communicate data on the environmental condition to a reader.

19 Claims, 15 Drawing Sheets

Related U.S. Application Data which is a continuation-in-part of application No. 15/455,795, filed on Mar. 10, 2017, now Pat. No. 10,155,360.

(60) Provisional application No. 62/306,995, filed on Mar. 11, 2016.

(56) References Cited

U.S. PATENT DOCUMENTS

| | | | |
|---|---|---|---|
| 6,632,550 B1 | 10/2003 | Yu et al. | |
| 6,893,752 B2 | 5/2005 | Veeramasuneni et al. | |
| 7,244,304 B2 | 7/2007 | Yu et al. | |
| 7,425,236 B2 | 9/2008 | Yu et al. | |
| 7,612,120 B2 | 11/2009 | Letts | |
| 7,651,564 B2 | 1/2010 | Francis | |
| 7,745,357 B2 * | 6/2010 | Smith | B28B 19/0092 442/386 |
| 7,758,980 B2 | 7/2010 | Yu et al. | |
| 7,861,488 B2 | 1/2011 | Giles et al. | |
| 7,964,034 B2 | 6/2011 | Yu et al. | |
| 8,070,895 B2 | 12/2011 | Engbrecht et al. | |
| 8,142,914 B2 | 3/2012 | Yu et al. | |
| 8,500,904 B2 | 8/2013 | Yu et al. | |
| 9,157,231 B2 | 10/2015 | Wingfield et al. | |
| 9,932,271 B2 * | 4/2018 | Teng | C04B 22/143 |
| 9,938,192 B2 * | 4/2018 | Moore | C04B 14/42 |
| 9,963,391 B2 * | 5/2018 | Abolt | B32B 7/12 |
| 9,991,596 B2 | 6/2018 | Rokhsaz et al. | |
| 2008/0213529 A1 | 9/2008 | Gray et al. | |
| 2010/0026457 A1 | 2/2010 | Holloway | |
| 2013/0204439 A1 * | 8/2013 | Scelzi | G06Q 10/00 700/276 |
| 2014/0361796 A1 | 12/2014 | Vokey et al. | |
| 2016/0204820 A1 * | 7/2016 | Mow | H04B 1/40 455/575.7 |
| 2016/0217664 A1 | 7/2016 | Bradford | |
| 2016/0267769 A1 * | 9/2016 | Rokhsaz | G06K 19/0717 |
| 2017/0138881 A1 * | 5/2017 | Krapf | G01N 33/383 |

* cited by examiner

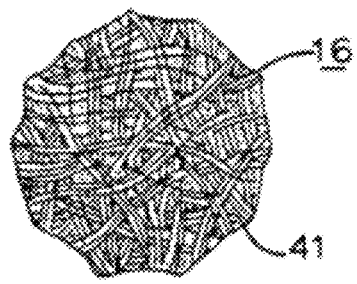
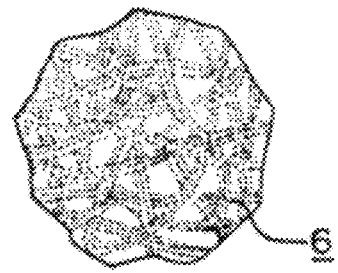
FIG.5  FIG.6
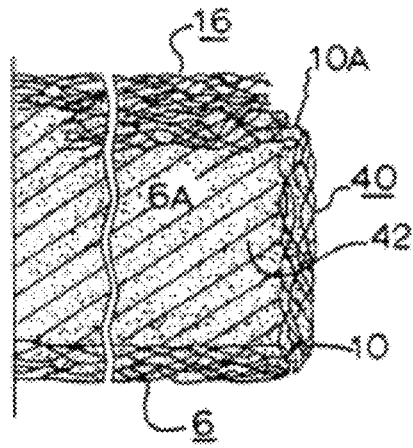
FIG.7
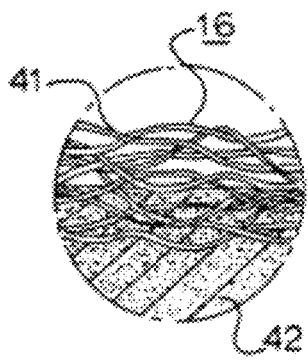
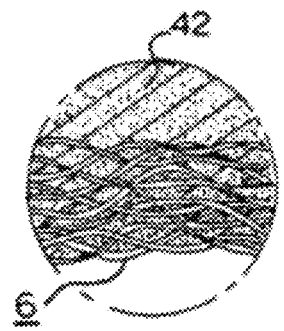
FIG.8  FIG.9

CONSTRUCTION PANELS, MATERIALS, SYSTEMS, AND METHODS

CROSS-REFERENCE TO RELATED APPLICATIONS

This application is a continuation-in-part of U.S. application Ser. No. 15/703,322, filed Sep. 13, 2017, which is a continuation-in-part of U.S. application Ser. No. 15/455,795, filed Mar. 10, 2017, which claims priority benefit of U.S. Provisional Application No. 62/306,995, filed on Mar. 11, 2016, the disclosures of which are incorporated by reference herein.

FIELD

The present disclosure relates generally to the field of panels and other materials for use in building construction, and more particularly to panels and other construction materials with environmental sensors, methods of making such panels, and systems for their use.

BACKGROUND

Interior wallboard, exterior building sheathing, flooring, roofing, and other building panels can be exposed to extreme environmental conditions including moisture, wind, and extreme temperatures during and after construction. Additionally, such systems may be installed improperly, such that seams between panels are not completely sealed. Furthermore, sheathing and roofing panels installed around windows, scuppers, parapet walls, and other openings and areas in the building may be particularly vulnerable to environmental damage.

When moisture intrusion and/or degradation or destruction of the panels occurs due to these conditions, it often goes unnoticed for a length of time, usually until visually observed. Moreover, leaks and/or degradation that may not be visible via typical inspection methods may never be detected. Thus, such damage conditions, as well as mold and mildew resulting from water infiltration, may intensify to easily avoidable levels because of the lack of early detection systems for these issues.

For example, in environments exposed to freezing temperatures, water leaking into a roofing or sheathing panel may undergo multiple freeze-thaw cycles and thereby cause separation of the panel core and the fiberglass mat facer and associated membrane (e.g., building wrap), if present. Once separation of the mat facer has occurred, wind uplifting causes further separation of the mat facer, sometimes resulting in billowing of the mat facer.

Accordingly, it would be desirable to provide construction panels and other construction materials having sensors for detecting environmental conditions in or on the panel/structure, to monitor and prevent damage to such materials.

In one aspect, building panels are provided, including a panel including a panel core and having a first surface and an opposed second surface, and at least one environmental sensor assembly associated with the panel core and configured to detect an environmental condition of the panel including moisture, pressure, or both, and wirelessly communicate data on the environmental condition to a reader, wherein the at least one environmental sensor assembly is self-supporting, passive, and includes an antenna, a processing module, and a wireless communication module.

In another aspect, systems for detecting an environmental condition at a panel are also provided, including at least one of the building panels and at least one reader for receiving the data wirelessly communicated from the at least one environmental sensor assembly.

In yet another aspect, methods of detecting an environmental condition are provided, including providing at least one of the building panels and wirelessly communicating data on the environmental condition from the at least one environmental sensor assembly to a reader.

In still yet another aspect, methods for manufacturing a building panel are provided, including combining a panel core slurry and a panel facing material to form a panel core having a first surface and an opposed second surface, the first surface being associated with the panel facing material, and disposing at least one environmental sensor assembly within the panel core slurry or between the panel core slurry and the panel facing material, wherein the at least one environmental sensor is configured to detect an environmental condition of the panel including moisture, pressure, or both, and wirelessly communicate data on the environmental condition to a reader, wherein the at least one environmental sensor assembly is self-supporting, passive, and includes an antenna, a processing module, and a wireless communication module.

BRIEF DESCRIPTION OF THE DRAWINGS

Referring now to the drawings, which are meant to be exemplary and not limiting, and wherein like elements are numbered alike. The detailed description is set forth with reference to the accompanying drawings illustrating examples of the disclosure, in which use of the same reference numerals indicates similar or identical items. Certain embodiments of the present disclosure may include elements, components, and/or configurations other than those illustrated in the drawings, and some of the elements, components, and/or configurations illustrated in the drawings may not be present in certain embodiments.

FIG. 5 is a fragmentary plan view taken as indicated by line 5-5 on FIG. 4;

FIG. 6 is a fragmentary bottom view taken as indicated by the line 6-6 on FIG. 4 and illustrating the bottom surface of the underlying mat of the board;

FIG. 7 is a transverse sectional view of an edge portion of the completed board, this view being taken as indicated by the line 7-7 on FIG. 4;

FIG. 8 is a further enlarged fragmentary sectional view taken as indicated toward the top of FIG. 4;

FIG. 9 is a further enlarged fragmentary sectional view taken as indicated toward the bottom of FIG. 4;

DETAILED DESCRIPTION

Figure 1:
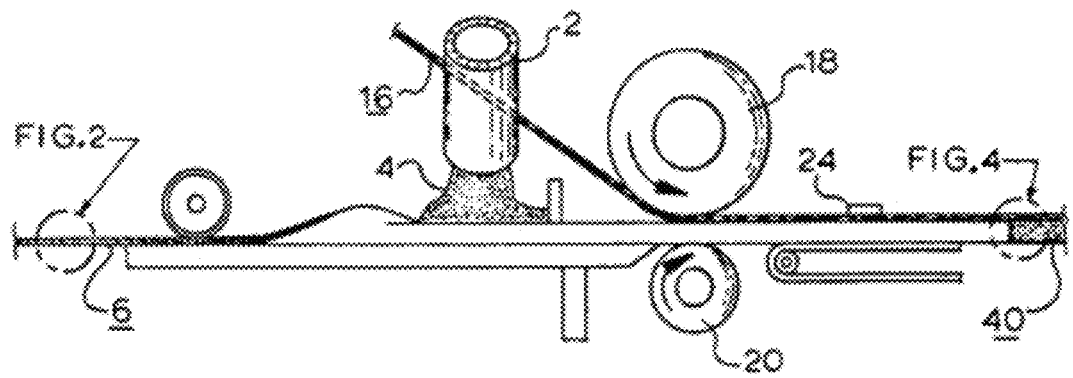
FIG. 1 is a diagrammatic, fragmentary side elevational view illustrating portions of a manufacturing line for producing gypsum board of a type suitable for use in the manufacture of gypsum panels prepared for use in accordance with the present disclosure.

Disclosed herein are building construction panels and materials, as well as methods of making and using such panels and materials, and systems for their use. The panels and materials described herein may be panels for internal or external construction applications, such as for wallboard, external sheathing, roof board, and flooring, sound mitigation and rain screen mats, and other construction applications. For example, the panels described herein may be external gypsum sheathing panels, such as those described in U.S. application Ser. Nos. 15/014,793 and 15/014,922, entitled "Gypsum Panels, Systems, and Methods," which are incorporated herein by reference in their entirety. For example, the panels described herein may be fiber-reinforced gypsum panels containing cellulosic fibrous material, such as those described in U.S. Pat. Nos. 6,893,752, 8,070,895, 6,342,284, 6,632,550, 7,244,304, 7,425,236, 7,758,980, 7,964,034, 8,142,914, and 8,500,904, which are incorporated by reference herein in their entirety. For example, the panels described herein may be roof deck panels, such as those described in U.S. Pat. No. 5,319,900, which is incorporated by reference herein in its entirety. For example, the panels described herein may be isocyanurate or similar insulation type panels, such as those described in U.S. Pat. No. 7,612,120, which is incorporated by reference herein in its entirety. For example, the panels described herein may be plywood, oriented strand board (OSB), or other wood-based panels known in the construction industries. For example, the construction materials described herein may be polymeric rain screen or sound mitigation mats, such as those described in U.S. Pat. Nos. 9,157,231 and 7,861,488, which are incorporated by reference herein in their entirety. For example, the panels or construction materials described herein may be gypsum and/or concrete flooring underlayments, such as those described in U.S. Pat. No. 7,651,564, which is incorporated by reference herein in its entirety. Overall, this disclosure is directed to various construction panels and materials for internal and/or external construction applications, for commercial and/or residential applications, in which the construction panels and/or materials contain environmental sensors configured for detecting one or more environmental conditions of the panel, material, or surrounding structure with which it is associated.

Construction Panels and Materials

Generally, the panels and other construction materials may include any suitable construction or configuration known in the industry. For example, the panels may be panels that contain gypsum as a significant component of the panel core (e.g., in amounts of up to 90 percent, by weight, or more) or may be panels that contain gypsum as a component of the panel core in combination with other components (e.g., in amounts of less than 90 percent). Examples of other components that may be present in the panel core include cellulose or other fibers. Furthermore, while the present disclosure is generally directed to building panels that include a gypsum core or layer, other panels may be suitably substituted for the gypsum panel, such as wood-based, foam-based, and other material-based panels that are suitable for the building construction purposes described herein. That is, while various embodiments of the present disclosure are described or illustrated with reference to a gypsum panel, it should be understood that the gypsum core and other panel features could be replaced with suitable components of these other panel or construction material types. In particular, such panels and other materials are described in the documents incorporated by reference herein. For example, these panels and mats may include any suitable panel core (e.g., one or more layers forming the structural core of the panel) along with any suitable facer material or other external coating material, as will be described herein.

Figure 23:
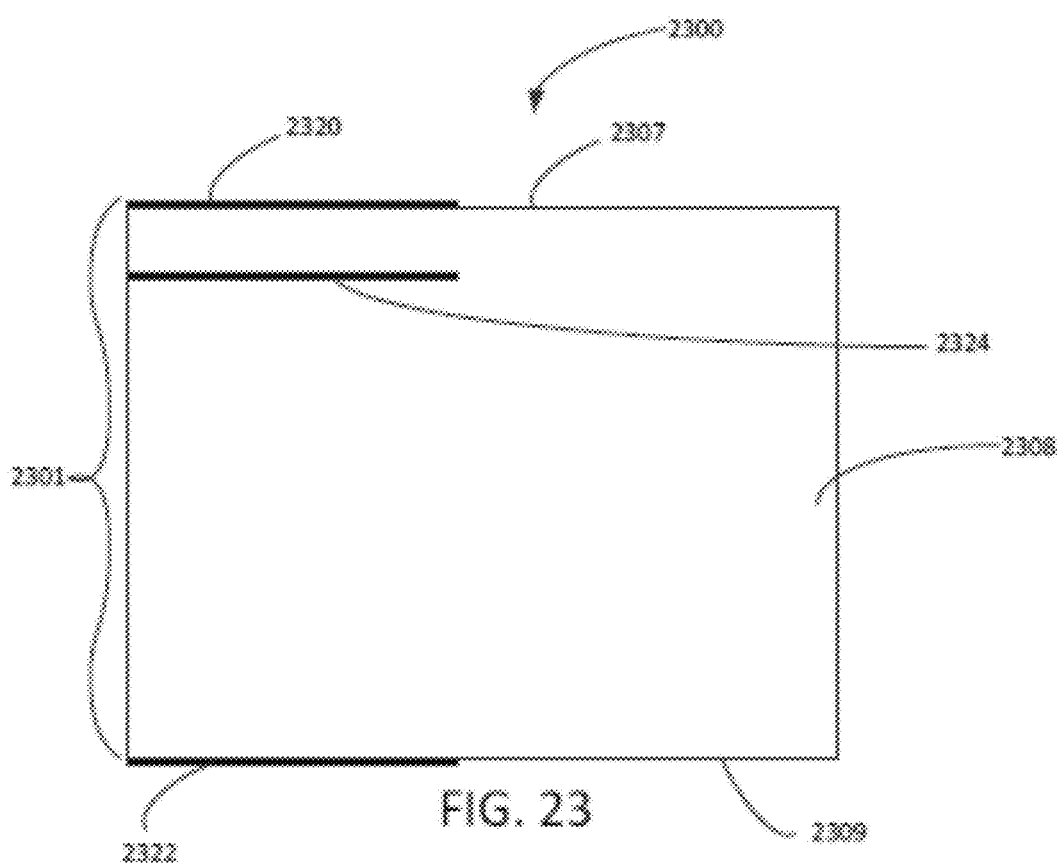
FIG. 23 is a cross-sectional view of a construction panel or material.

In certain embodiments, as shown in FIG. 23, a building panel 2300 includes a panel (e.g., a panel core 2301 formed of a one or more layers of a panel core material 2308, with or without a facer material) having a first surface 2307 and an opposed second surface 2309, and an environmental sensor assembly 2320, 2322, 2324 associated with the panel 2300 and configured to detect an environmental condition of the panel 2300 and wirelessly communicate data on the environmental condition to a reader, wherein the environmental sensor assembly is self-supporting and comprises an antenna, a processing module, and a wireless communication module. For example, as discussed above, the panel may be selected from a gypsum panel, a fiber-reinforced gypsum panel, an isocyanurate panel, a wood-based panel, or other known construction panels. For example, a construction material may also be provided, such as various construction mats or other structures including, but not limited to, a polymeric rain screen, a polymeric sound mitigation mat, and a polymeric roofing drainage mat, having an environmental sensor assembly associated therewith. For example, such mats may be rolled materials that are cut to size as needed. As shown in FIG. 23, the environmental sensor assembly (various assemblies illustrated, shown as 2320, 2322, 2324) may be positioned in or on any suitable surface (internal or external) of the panel or material. For example, the environmental sensor assembly may be disposed on an external surface or edge of the panel or within or on a surface of the panel. For example, in panels having a facer material, a panel coating, or multiple layers forming the panel core, the environmental sensor assembly may be disposed internally, i.e., between two layers of the panel.

For example, in a gypsum panel, such as a fiber-reinforced gypsum panel, the environmental sensor assembly may be disposed on an external surface or edge of the panel or within or on a surface of the panel. For example, in gypsum panels having a facer material, a panel coating, or multiple layers forming the panel core, the environmental sensor assembly may be disposed internally, i.e., between two layers of the panel. Thus, in certain embodiments, a building panel includes a panel core and at least one environmental sensor assembly associated with the panel core. For example, in isocyanurate panels, the environmental sensor assembly may be disposed on an external surface or edge of the panel or within, such as between various layers of, or on a surface of the panel. For example, in wood-based panels, the environmental sensor assembly may be disposed on an external surface or edge of the panel or within, such as between various layers of, or on a surface of the panel. For example, in a polymeric mat, such as a sound mitigation mat, roofing drainage mat, or rain screen, the environmental sensor assembly may be disposed on an external surface or between various layers of the mat.

Figure 24:
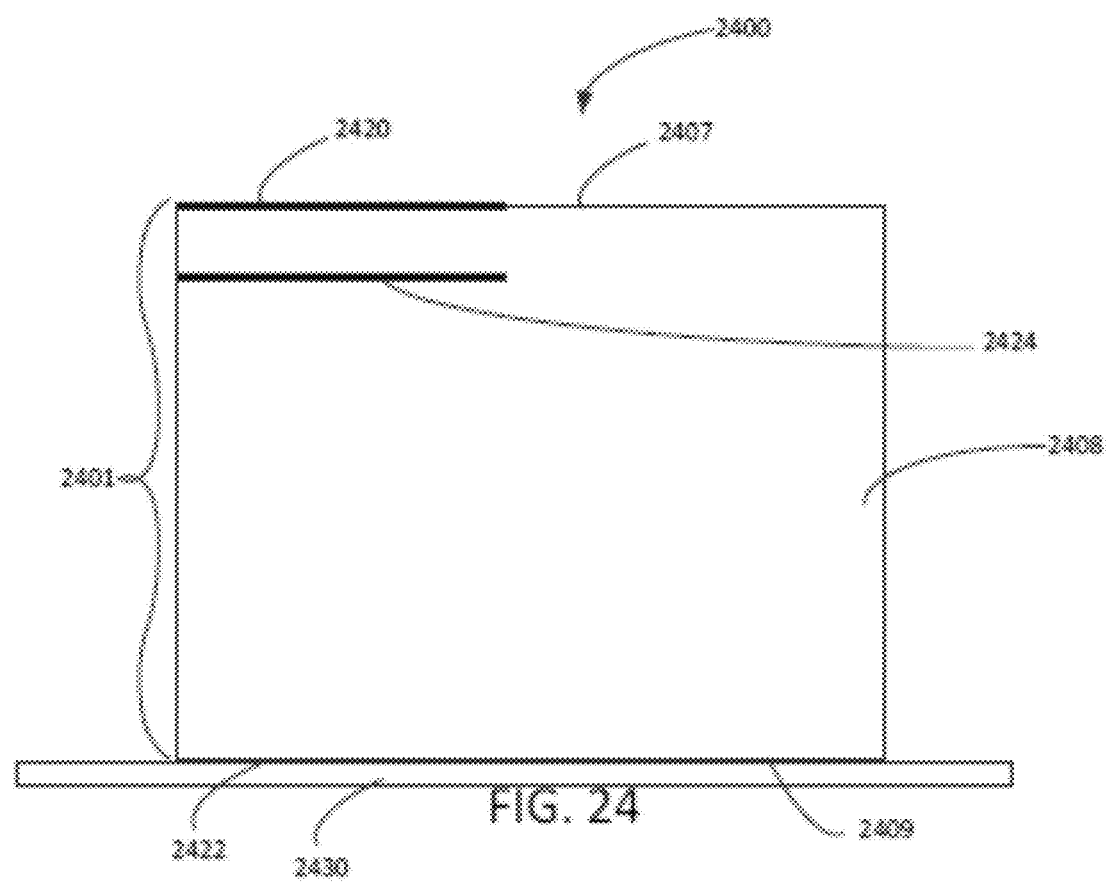
FIG. 24 is a cross-sectional view of a flooring underlayment.

In certain embodiments, as shown in FIG. 24, a flooring underlayment 2400 is provided, and includes a gypsum and/or concrete underlayment material 2401 (e.g., a pour-in-place or other suitable underlayment material configuration formed of one or more layers of underlayment material 2408 on a floor substrate 2430) and an environmental sensor assembly 2420, 2422, 2424 associated with the underlayment material and configured to detect an environmental condition of the underlayment and wirelessly communicate data on the environmental condition to a reader, wherein the environmental sensor assembly is self-supporting and comprises an antenna, a processing module, and a wireless communication module. For example, the underlayment may have a first surface 2407 and an opposed second surface 2409. For example, the environmental sensor assembly 2420, 2422, 2424 may be disposed within or on a surface of the gypsum and/or concrete underlayment material.

Figure 17:
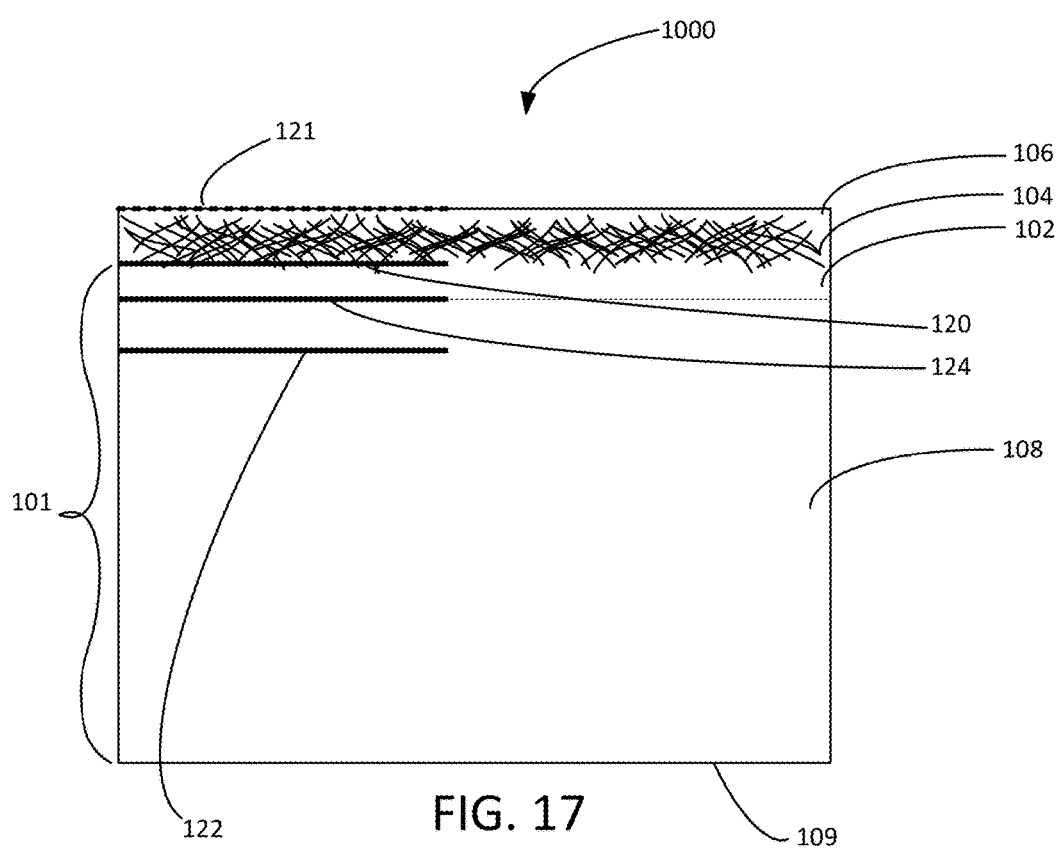
FIG. 17 is a cross-sectional view of a construction panel.

In certain embodiments, as shown in FIG. 17, a panel 1000 includes a panel core 101 having a first surface and a second opposed surface, and a first facer material 104 associated with the first surface of the panel core 101. For example, the facer material may be any suitable facer material known in the art, including paper and fibrous facer materials. In certain embodiments, as shown in FIG. 17, the facer material 104 is a fibrous material, such as fiberglass. Thus, while certain embodiments herein are described with reference to a fiberglass mat, it should be understood that any suitable paper facer or other fibrous mat material may be substituted and fall within the scope of the disclosure.

In certain embodiments, as shown in FIG. 17, a gypsum panel 1000 includes a gypsum core 101 having a first surface and a second opposed surface, and a first facer material 104 associated with the first surface of the gypsum core 101. For example, the facer material may be any suitable facer material known in the art, including paper and fibrous facer materials. In certain embodiments, as shown in FIG. 17, the facer material 104 is a fibrous material, such as fiberglass. Thus, while certain embodiments herein are described with reference to a fiberglass mat, it should be understood that any suitable paper facer or other fibrous mat material may be substituted and fall within the scope of the disclosure.

In certain embodiments, the facer material is a nonwoven fibrous mat formed of fiber material that is capable of forming a strong bond with the material of a building panel core through a mechanical-like interlocking between the interstices of the fibrous mat and portions of the core material. Examples of fiber materials for use in the nonwoven mats include mineral-type materials such as glass fibers, synthetic resin fibers, and mixtures or blends thereof. Both chopped strands and continuous strands may be used.

In certain embodiments, the facer material is a nonwoven fiberglass mat. For example, the glass fibers may have an average diameter of from about 1 to about 17 microns and an average length of from about ¹⁄₁₆ inch to about 1 inch. For example, the glass fibers may have an average diameter of 13 microns (i.e., K fibers) and an average length of ¾ inch. In certain embodiments, the non-woven fiberglass mats have a basis weight of from about 1.5 pounds to about 4.0 pounds per 100 square feet of the mat. The mats may each have a thickness of from about 10 mils to about 50 mils. The fibers may be bonded together to form a unitary mat structure by a suitable adhesive. For example, the adhesive may be a urea-formaldehyde resin adhesive, optionally modified with a thermoplastic extender or cross-linker, such as an acrylic cross-linker, or an acrylate adhesive resin.

Figure 2:
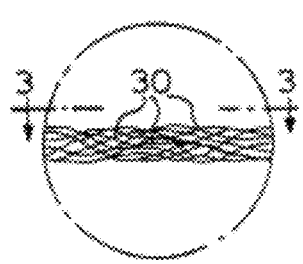
FIG. 2 is an enlarged fragmentary sectional view, taken as indicated toward the left of FIG. 1, of an underlying fiber glass mat used in the manufacture of the gypsum board.
Figure 3:
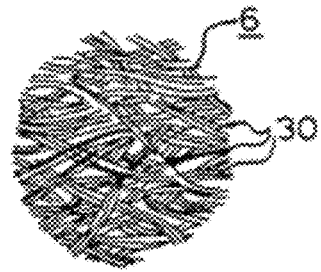
FIG. 3 is a fragmentary plan view taken as indicated by the line 3-3 on FIG. 2.
Figure 4:
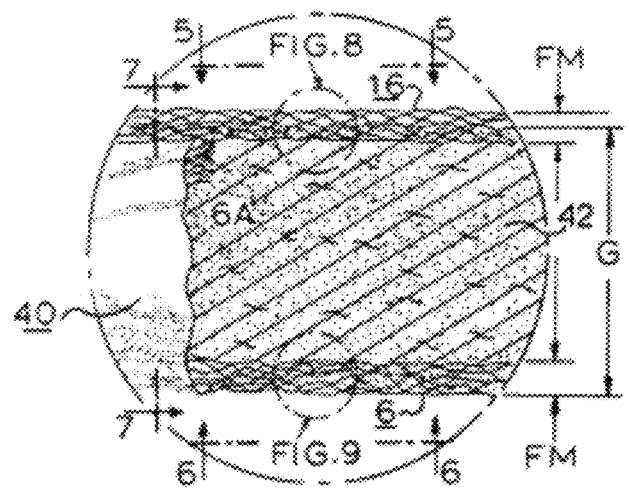
FIG. 4 is an enlarged sectional view taken as indicated toward the right on FIG. 1 and illustrating both underlying and overlying fiber glass mats, with intervening gypsum composition, used in the manufacture of the board.

In certain embodiments, as shown in FIGS. 2 and 3, facer material mats 6 and 16, contain glass fiber filaments 30 oriented in random pattern and bound together with a resin binder (not shown). One embodiment of glass fiber mat-faced gypsum board 40 is shown in FIGS. 4 and 7, in which the set gypsum of the core 42 penetrates substantially through the thickness of the mat 6 over substantial area portions thereof and in which the set gypsum of the core 42 penetrates the mat 16 partially, with the surface being thus substantially free of set gypsum. The gypsum-free surface of mat 16, as seen in FIG. 8, is highly textured, and provides an excellent substrate for adhering thereto an overlying component inasmuch as it contains many interstices into which an adhesive composition can flow and bond.

In certain embodiments, the panels have a thickness from about ¼ inch to about 1 inch. For example, the panels may have a thickness of from about ½ inch to about ⅝ inch.

In some embodiments, as shown in FIG. 17, gypsum crystals of the gypsum core 101 penetrate a remaining portion of the first fiberglass mat 104 such that voids in the first fiberglass mat 104 are substantially eliminated and the water resistance of the panel 1000 is further enhanced. For example, in one embodiment, the first fiberglass mat 104 has a continuous barrier coating 106 on a surface opposite the gypsum core 101, the continuous barrier coating 106 penetrating a portion of the first fiberglass mat 104, to define the remaining portion of the first fiberglass mat 104. That is, gypsum crystals of the gypsum core 101 penetrate a remaining fibrous portion of the first fiberglass mat 104 such that voids in the first fiberglass mat 104 are substantially eliminated. As used herein the phrase "such that voids in the fiberglass mat are substantially eliminated" and similar phrases refer to the gypsum slurry (e.g., slate coat) filling all or nearly all of the interstitial volume of the fiberglass mat that is not filled by the coating material.

As used herein, the term "continuous barrier coating" refers to a coating material that is substantially uninterrupted over the surface of the fibrous mat. The continuous barrier coating on the external surface of the facer may be any suitable coating known in the art. For example, the coating may include a binder material and, optionally, a filler. For example, the coating may include a polymer or resin based binder material along with one or more inorganic fillers.

In certain embodiments, as shown in FIG. 17, the gypsum core 101 includes two or more gypsum layers 102, 108, while in other embodiments the gypsum core includes a single gypsum layer. For example, the gypsum core may include various gypsum layers having different compositions. In some embodiments, the first gypsum layer 102 that is in contact with the fiberglass mat 104 (i.e., the layer that forms an interface with the coating material and at least partially penetrates the remaining fibrous portion of the first fibrous mat) is a slate coat layer. In some embodiments, the first gypsum layer 102 is present in an amount from about 2 percent to about 20 percent, by weight, of the gypsum core 101. The various gypsum layers are shown as separate layers in the figures for ease of illustration; however, it should be understood that overlap of these materials may occur at their interfaces.

The layers of the gypsum core may be similar to gypsum cores used in other gypsum products, such as gypsum wallboard, drywall, gypsum board, gypsum lath, and gypsum sheathing. For example, the gypsum core may be formed by mixing water with powdered anhydrous calcium sulfate or calcium sulfate hemihydrate, also known as calcined gypsum, to form an aqueous gypsum slurry, and thereafter allowing the slurry mixture to hydrate or set into calcium sulfate dihydrate, a relatively hard material. In certain embodiments, the gypsum core includes about 80 weight percent or above of set gypsum (i.e., fully hydrated calcium sulfate). For example, the gypsum core may include about 85 weight percent set gypsum. In some embodiments, the gypsum core includes about 95 weight percent set gypsum. The gypsum core may also include a variety of additives, such as accelerators, set retarders, foaming agents, and dispersing agents.

Figure 18:
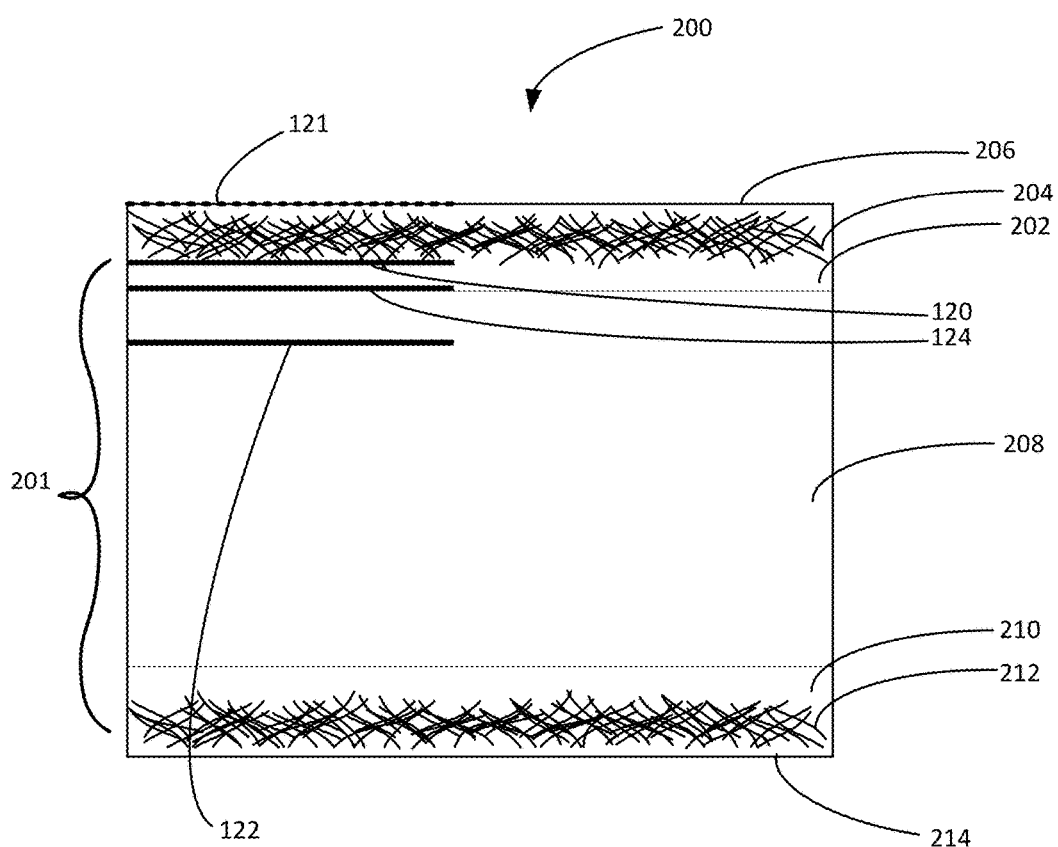
FIG. 18 is a cross-sectional view of a construction panel.

In certain embodiments, as shown in FIG. 18, a gypsum panel 200 includes two facers 204, 212 that are associated with the gypsum core 201. As with the first facer material, the second facer material may be any suitable facer material, such as paper or fibrous materials. In certain embodiments, both facers 204, 212 are fiberglass mats. The second fiberglass mat 212 is present on a face of the gypsum core 201 opposite the first fiberglass mat 204. In some embodiments, only the first fiberglass mat 204 has a continuous barrier coating 206 on a surface thereof. In other embodiments, both fiberglass mats 204, 212 have a coating 206, 214 on a surface thereof opposite the gypsum core 201. In some embodiments, the gypsum core 201 includes three gypsum layers 202, 208, 210. One or both of the gypsum layers 202, 210 that are in contact with the fiberglass mats 204, 212 may be a slate coat layer.

As shown in FIG. 17, gypsum panels according to the present disclosure may have a first surface 107 of the panel 1000 formed by the first facer material 104 and/or a continuous barrier coating 106 thereon. The gypsum panel 1000 also has a second surface 109 of the panel opposite the first surface 107.

In certain embodiments, as shown in FIGS. 10-14 and 21-22, the panel may be a roof deck panel. For example, installation of a roof deck system in construction of a building, generally involves constructing a frame for support of the roof of a building; affixing to the frame corrugated sheets to provide a surface for support of the other components of the roof deck system; affixing to the corrugated sheets planar support members; and affixing to the planar support members an exterior finishing material having good weathering properties. Roof deck systems which include panels of insulation sandwiched between the aforementioned corrugated sheets and planar support members are used widely also. Such systems are designed to be insulative in character and weather resistant. Such roof deck systems can be used to advantage to conserve energy used for heating and to conserve energy used for air-conditioning. More specifically, such roof deck systems typically include corrugated metal sheets which are mechanically affixed, usually by screws or bolts, to appropriate structural members of the building such as steel beams. The corrugated metal sheets support the weight of the components which overlie it, including the insulating material (when used), the planar support members, and the finishing material. Light weight, low density insulating panels such as expanded polystyrene, polyisocyanurate, and the like, are used widely in such systems, especially in colder climates. The planar support members generally include gypsum boards and are fastened in place by mechanical fasteners such as screws to the underlying corrugated metal sheet. When panels of insulation are used, they are sandwiched between the underlying corrugated metal sheets and the overlying panels of gypsum board. An exterior finishing material, such as a polymeric or rubber membrane or alternating layers of asphalt and roofing felt, overlies the panels of gypsum board.

Figure 10:
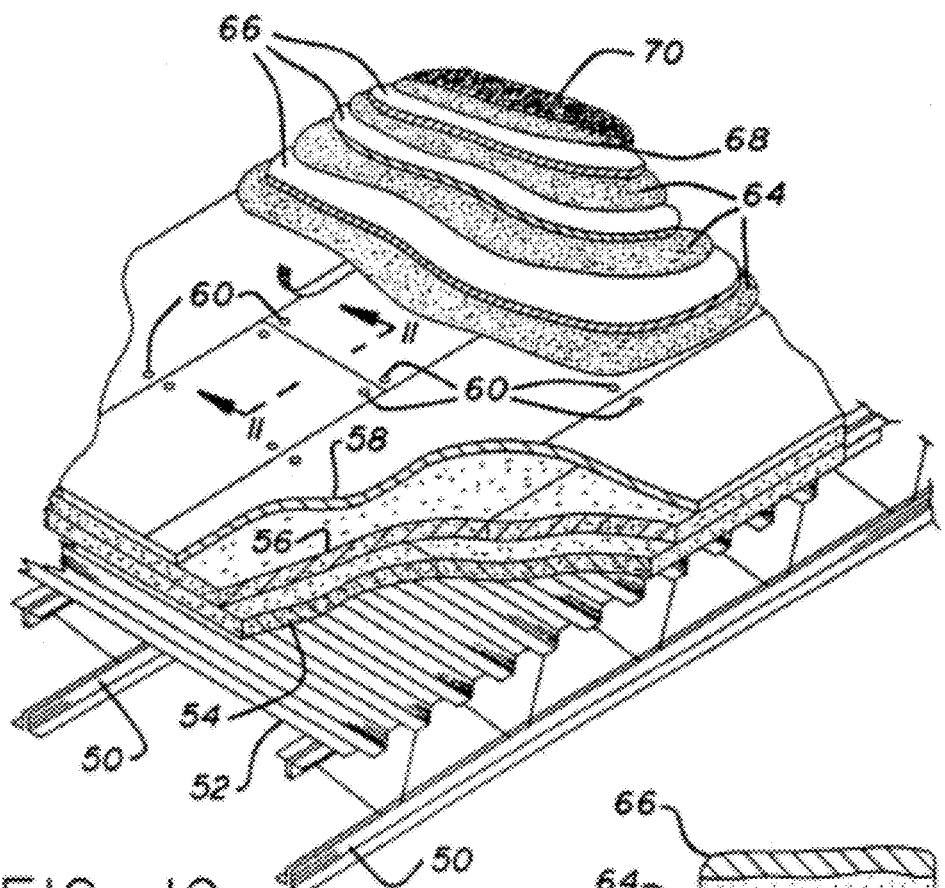
FIG. 10 is a perspective view partly broken away and in section of an exemplary roof deck system incorporating a panel in accordance with the present disclosure.

A typical roof deck system incorporating the fibrous mat-faced gypsum board as described above is shown in FIGS. 10 to 12. In this construction, spaced parallel trusses 50 extending between building support members (not shown) support a corrugated metal deck 52 which is welded or otherwise fastened to the trusses. Layers 54 and 56 of insulating sheet material, which may, for example, be of polyisocyanurate, are disposed on the corrugated metal deck. A layer 58 of fibrous mat-faced gypsum board panels of the type described hereabove are secured to the corrugated deck 52 by means of fasteners 60 passing therethrough and through the underlying insulation layers 54 and 56 into the deck 52. The joints of the panel layer 58 are sealed by application of tape 62, as shown in FIG. 10 with respect to one of the panel joints. Overlying the gypsum layer 58 is a waterproof roofing membrane including alternate layers of asphalt 64 and roofing felt 66, three layers of each being shown in the present example. A final coating of asphalt 68 is covered with a crushed gravel topping layer 70.

Figure 12:
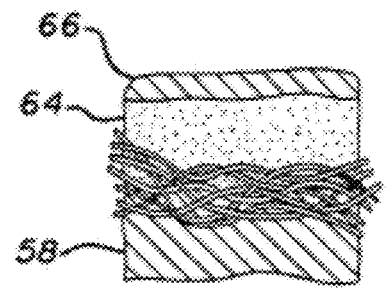
FIG. 12 is a greatly enlarged sectional view of the circled area of FIG. 11 showing the penetration of the first asphalt layer into the fibrous upper surface of the panel in accordance with the disclosure.
Figure 11:
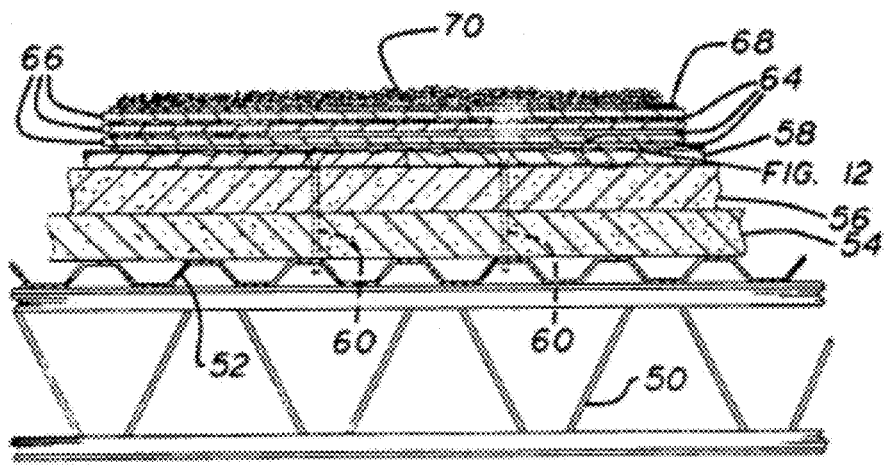
FIG. 11 is an enlarged sectional view taken along line 11-11 of FIG. 10.

In the enlarged view of FIG. 12, the manner in which the first asphalt layer 64 penetrates into the upwardly facing fibrous mat-face of the gypsum board panel layer 58 is illustrated. This penetration assures a secure adhesion of the waterproof membrane to the structural layers of the roof system.

Figure 21:
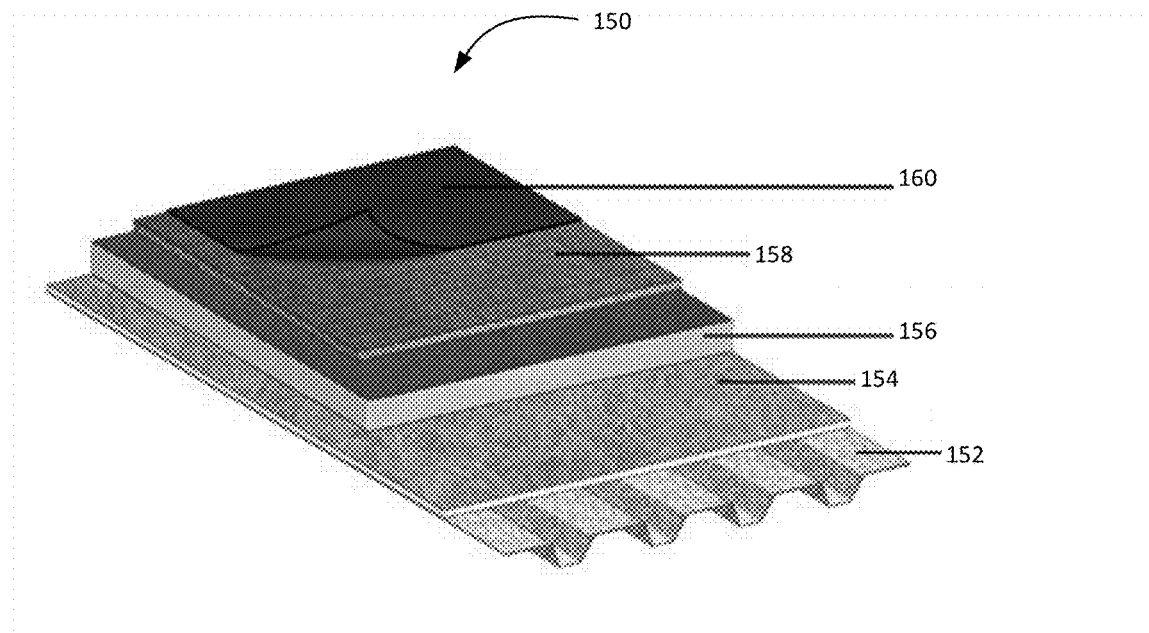
FIG. 21 is a perspective view of a roof deck assembly.
Figure 22:
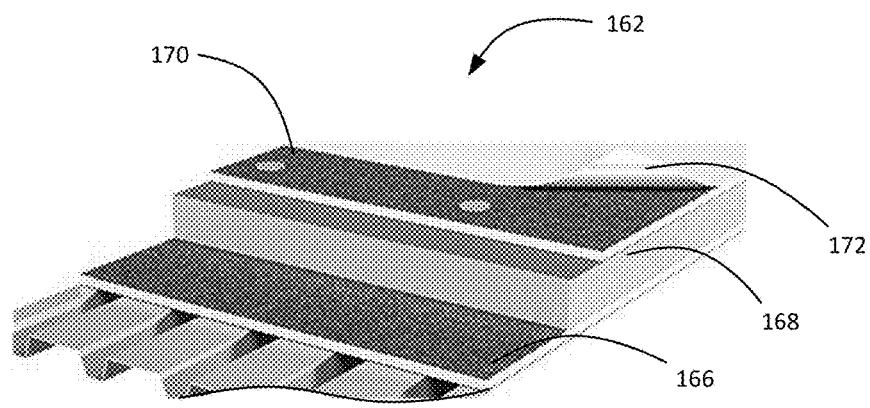
FIG. 22 is a partial perspective view of a roof deck assembly.

In some embodiments, as shown in FIG. 21, the roof deck system 150 incorporating the gypsum panels having the environmental sensor assembly includes a gypsum roof board/panel, as an overlayment 158, underlayment 154, or both, as well as insulation 156, and a roof covering or membrane 160, mounted on a steel, wood, or other roof deck 152 (shown as steel). In some embodiments, as shown in FIG. 22, the roof deck system 162 incorporating the gypsum panels having the environmental sensor assembly is a single-ply membrane system. For example, the system may include at least one gypsum roof panel 166, 170, insulation 168, and a single-ply membrane 172 (e.g., EPDM or thermoplastic membrane). Various embodiments of such roofing systems utilizing gypsum roofing panels are known in the art and the present disclosure is meant to encompass any such suitable system configurations or designs incorporating the gypsum panels disclosed herein. For example, the roofing system may incorporate suitable asphalt, EPDM, Turbo Seal, CSPE, Modified Bitumen, PVC, cold liquid membranes, FTPO, TPO, coal-tar pitch built up, or other built up roof constructions, among others.

Figure 13:
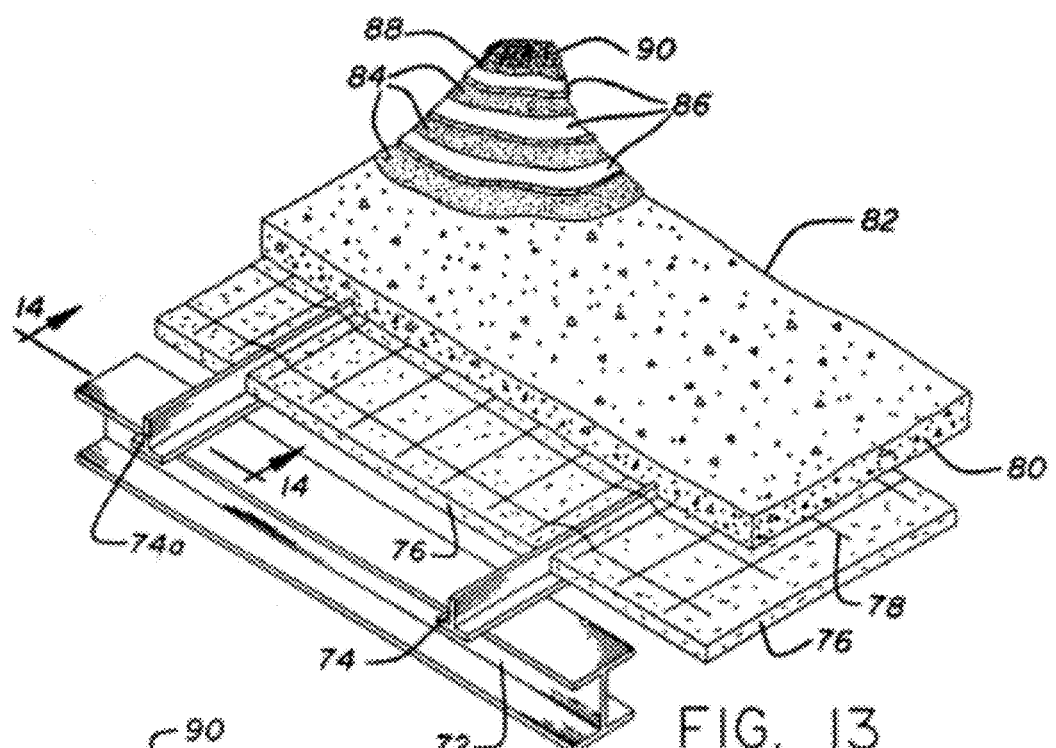
FIG. 13 is a perspective view of another type of roof system incorporating the panel in accordance with the disclosure as the primary support layer.
Figure 14:
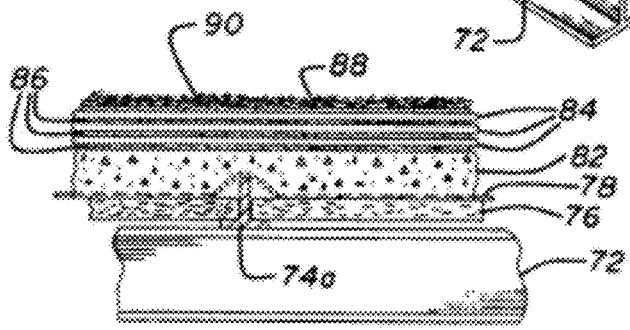
FIG. 14 is a sectional view taken along line 14-14 of FIG. 13.

Referring to FIGS. 13 and 14, a poured-in-place roof deck system is shown including purlins 72 supporting spaced sub-purlins (bulb tees 74 in parallel spaced relation). Fibrous mat-faced gypsum board panels 76 of the type described above are supported on the horizontal flanges 74a of the sub-purlins 74. A reinforcing mesh screen 78 is laid over the sub-purlins and gypsum board panels 76 and a layer of settable gypsum slurry 80 is poured in place over the reinforcing mesh. The slurry 80 is allowed to harden to form a smooth continuous deck surface 82. Adhesion of the slurry to the gypsum board panel 76 is assured by the penetration of the slurry into the upwardly facing fibrous mat surface of the panels. A roofing membrane including alternate layers of asphalt 84 and roofing felt 86, three layers of each in the illustrated example, is applied to the surface 82. A final layer of asphalt 88 is covered with a coating of crushed rock or gravel 90.

Figure 16:
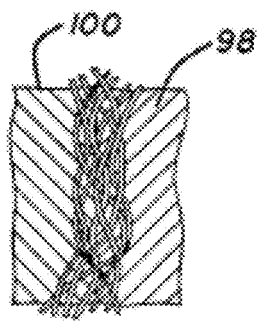
FIG. 16 is a greatly enlarged view of the circled portion of FIG. 15 showing the penetration of the plaster layer into the fibrous surface of the panel.
Figure 15:
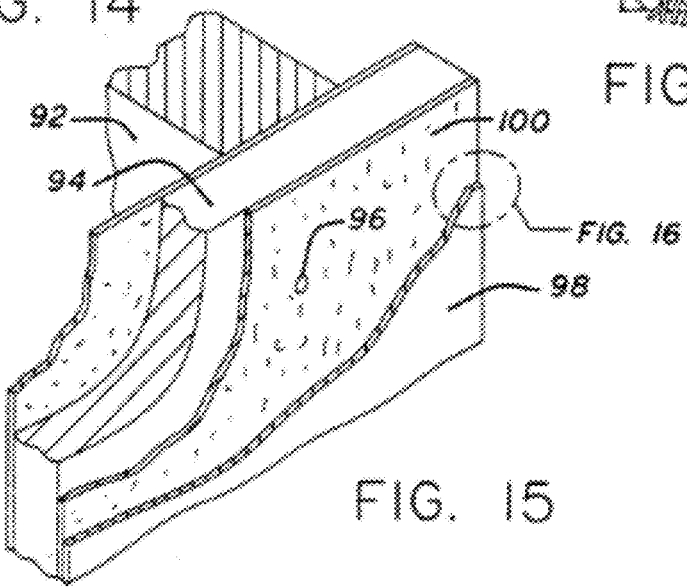
FIG. 15 is a perspective view partly broken away and in section of a composite wall structure employing the panel in accordance with the disclosure.

As regards interior finishing systems for use in a building, installation of such a system generally involves constructing a frame for support of the interior walls of a building; and affixing to the frame planar support members which provide a smooth continuous surface to support an interior finishing material having aesthetic and durability properties. Such systems are designed to be strong and durable and to withstand abuse during the building's occupancy. An example of an interior usage of the present fibrous mat-faced panel is illustrated in FIGS. 15 and 16. In these views, an interior wall system includes spaced vertical studs 92 to which fibrous mat-faced gypsum board panels 94 are attached by spaced fasteners 96 such as screws or nails. A thin layer 98 of plaster is applied to the fibrous mat surface 100 of the panel 94 and is troweled to form a smooth finish surface which may then be decorated by paint, paper or the like in a conventional manner. As shown in the enlarged view of FIG. 16, the plaster 98 penetrates into the fibrous mat surface of the panel 94 to effect a secure mechanical bond of the plaster layer to the panel. Although shown in the context of a wall in FIG. 15, the panel 94 may equally suitably be used as a ceiling panel and can be used with either a wood or metal stud support system. For some applications, it may be found that adjustments need to be made in the water-resistant properties of the core in order to obtain a satisfactory plaster finish.

In exterior systems, sheathing panels can be affixed to an underlying support member in any suitable way, for example, by the use of nails or screws. In such systems, the underlying support member may include, for example, panels of rigid plastic or metal sheets, for example, in corrugated form, purlins and sub-purlins. Panels of insulating material may be affixed to such support members and underlie panels of said panels, which are affixed thereto. The support member is typically affixed to the frame of the building.

In certain embodiments, as shown in FIGS. 17 and 18, the gypsum panel includes at least one environmental sensor assembly 120, 122, 124 associated with the gypsum panel. Although three environmental sensor assemblies are shown in FIGS. 17 and 18, it should be understood that a sensor assembly may alternatively be provided at one, two, or all of these locations, as well as at other locations in and on the gypsum panel. Additionally, as is discussed in further detail below, a plurality of environmental sensor assemblies may be provided, approximately equally spaced from one another at similar positions along the length of a panel (e.g., every 1, 2, or 3 feet).

In one embodiment, the environmental sensor assembly is disposed on the first surface of the panel. In one embodiment, the environmental sensor assembly is disposed on the second surface of the panel. For example, the first surface of the panel may be the external-facing surface of the panel upon installation, while the second surface of the panel may be the internal-facing surface of the panel upon installation. In other embodiments, the environmental sensor assembly is disposed at an external edge of the panel. In other embodiments, the environmental sensor assembly 120, 122, 124 is disposed within or at a surface of the panel core. For example, the environmental sensor assembly may be positioned on or adjacent the facer material or in another portion of the core material of the panel core, such as in the slate coat or another of the gypsum layers in a gypsum panel. For example, sensor assembly 120 is disposed between the first surface of the panel core 101/201 and the facing material (e.g., fibrous mat 104). For example, sensor assembly 122 is embedded with the body of the panel core 101/201. For example, sensor assembly 124 is disposed between the first and second gypsum layers 102 and 108/202 and 208 forming the panel core 101/201. In other embodiments, the environmental sensor assembly may be disposed on the surface of the facer material that receives a continuous barrier coating. Thus, the environmental sensor assembly may be disposed at any suitable position on or in the panel, depending on the desired location and type of environmental condition detection and the particular application of the panel.

In certain embodiments, the environmental sensor assembly is configured to detect an environmental condition of the panel or material with which it is associated and to communicate data regarding the environmental condition to a reader. For example, the environmental sensor assembly configured to detect one or more environmental conditions such as moisture, temperature, and/or pressure.

In certain embodiments, the environmental sensor assembly is self-supporting and includes a substrate on which an antenna, a processing module, and a wireless communication module are disposed. As used herein, the term "self-supporting" refers to the sensor assembly being operable to sense the target environmental conditions as a standalone assembly, without the need for a wired connection external to the sensor assembly. As such, the environmental sensor assemblies disclosed herein may advantageously be incorporated into panels or other materials at a variety of positions throughout the panel during manufacturing or at a construction site, without the need for additional labor or materials to wire or programs the sensors. In certain embodiments, the environmental sensor assembly is a passive system. As used herein, the term "passive system" refers to the sensor assembly having no battery and instead using the radio energy transmitted by a reader to power the assembly. Advantageously, passive systems may be used in applications where the panels, materials, and/or sensor assemblies are largely inaccessible, making replacement of the assembly or a battery associated therewith impossible without damaging the building or building envelope. Moreover, because passive systems have no power source and often no moving parts, these assemblies may have an extremely long lifespan that is at least equal to the typical lifespan of panels or other construction materials. In other embodiments, the environmental sensor assembly is an active system that includes an integrated power source, such as a battery, for example a rechargeable battery, such as one powered by solar power.

In certain embodiments, the environmental sensor assembly is a passive, ultra high frequency single-chip sensor inlay system. In certain embodiments, the antenna is a resistor/inductor/capacitor (RLC) tuned circuit operable to convert the environmental condition into an impedance change, and the processing module is coupled to the antenna and is operable to translate the impedance change into a sensor code by matching antenna impedance to die impedance. Thus, whereas traditional sensors exploit changes in resistance to measure environmental variables, which results in reduced tag read range due to power dissipated in the resistance, the present sensor assemblies' ability to use inductance or capacitance beneficially avoids issues with read range.

For example, the antenna may have an antenna impedance operable to vary based on the environmental condition. The processing module may be coupled to the antenna and include a tuning module operable to (i) vary a reactive component impedance in order to change a system impedance including the antenna impedance and the reactive component impedance, and (ii) produce an impedance value representative of the reactive component impedance. The wireless communication module may be coupled to the processing module and operable to communicate the impedance value representative of the reactive component impedance to the reader, which represents the data on the environmental condition. In some embodiments, the environmental sensor assembly also includes a memory module operable to store the impedance value representative of the reactive component impedance.

Figure 20:
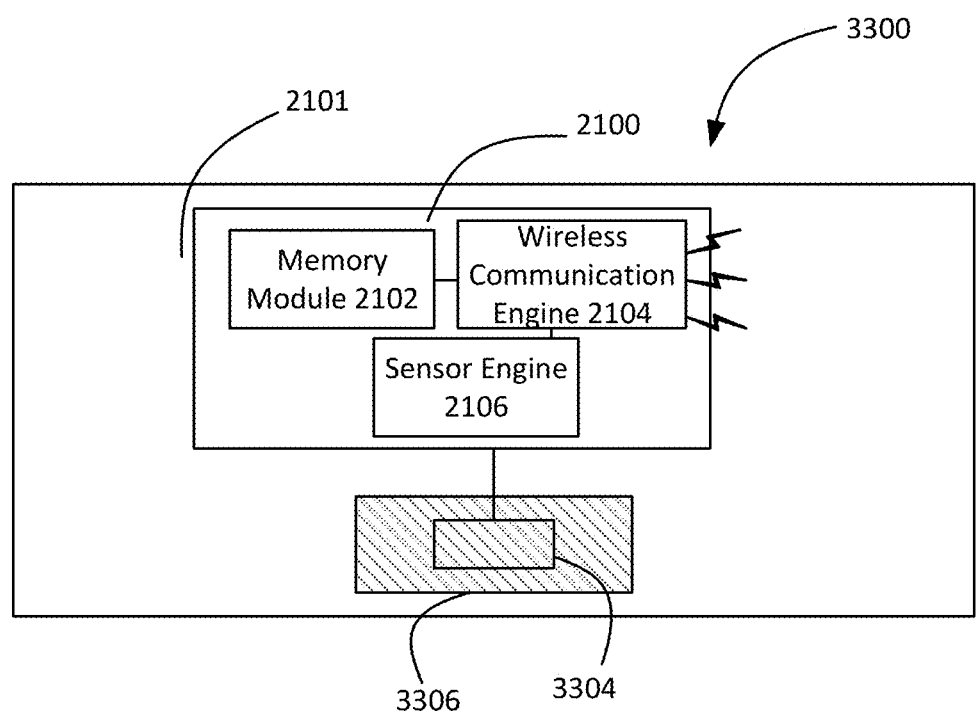
FIG. 20 is a plan view of an environmental sensor assembly.

For example, the sensor assembly may be a passive radio frequency identification (RFID) sensor, such as the sensor described in PCT Application Publication No. WO2015/184460, which is incorporated by reference in its entirety herein. As shown in FIG. 20, this passive RFID sensor includes an antenna, a processing module, and a wireless communication module. The antenna has an antenna impedance that may vary with the environment in which the antenna is placed. The processing module couples to the antenna and has a tuning module that may vary a reactive component impedance coupled to the antenna in order to change a system impedance that includes both the antenna impedance and the reactive component impedance. The tuning module then produces an impedance value representative of the reactive component impedance. A memory module may store the impedance value which may then later be communicated to an RFID reader via the wireless communication module. The RFID reader may then exchange the impedance value representative of the reactive components of impedance with the RFID reader such that the RFID reader or another external processing unit may process the impedance value in order to determine environmental conditions at the antenna.

FIG. 20 is a view of one embodiment of an RFID moisture or humidity sensing tag 3300. Moisture or humidity sensing tag 3300 is a passive RFID tag having a substrate 2101, on which is disposed an integrated circuit (IC) 2100. IC 2100 includes a memory module 2012, a wireless communication engine 2104, and a sensor engine 2106, which includes an antenna. IC 2100 is capable of sensing a change in the environmental perimeters proximate to IC 2100 via impedance changes associated with the antenna. Memory module 2102 is coupled with both the wireless communication engine 2104 and the sensor engine 2106. Memory module 2102 is capable of storing information and data gathered by sensor engine 2106 and communicated via wireless communication engine 2104. Further, wireless communication engine 2104 and sensor engine 2106 may be fully programmable via wireless methods.

The sensor impedance varies as the coupling of interdigitated capacitor 3304 responds to environmental changes. In one embodiment, interdigitated capacitor 3304 is located proximate to a film 3306 applied above interdigitated capacitor 3304. Film 3306 may be a material having an affinity for water (i.e., moisture or humidity) or other fluids, such as CO, $CO_2$, Arsenic, $H_2S$ or other known toxins or gases of interest. When film 3306 absorbs a fluid such as those described previously, the dielectric constant proximate to the interdigitated capacitor 3304 changes causing an impedance change. The impedance of the interdigitated capacitor 3304 sensed by the processing module coupled to the sensor then produces an output, a sensor code, representative of the absorbed material within film 3306. This data may be stored within a memory circuit of IC 2100 or transmitted to an external reader by the wireless communication module of IC 2100.

Thus, in certain embodiments, when configured as a moisture sensor, the sensor assembly measures the presence of water when the surrounding environment becomes wet. The interdigitated capacitor experiences a significant change in capacitance, when it changes from dry to wet; the dipole antenna registers an impedance change depending on the amount of water on the capacitor; and the sensor IC converts this into a code that indicates the amount of water present.

Advantageously, the sensor assemblies described herein may have a small size, such as approximately 4 inches by 1 inch, and be very thin, so as to provide nominal additional thickness when applied externally to the panel or construction material.

In certain embodiments, as shown in FIGS. 17 and 18, the building panel contains at least one environmental sensor assembly 120, 122, 124, that is embedded or disposed within the panel (e.g., between the surface of the core and the facing material, between layers forming the panel core, or within the body of the panel core). In such embodiments, the panel may further have at least one visual indicator 121 positioned on the first external surface of the panel (e.g., on surface coating 106/206), with each of the at least one visual indicators indicating a location of an environmental sensor assembly within the panel. That is, the visual indicator 121 may be positioned on the surface of the panel in line with one or more sensor assemblies embedded at the panel core. The visual indicator 121 may be any suitable marking, indentation, raised feature, etc. For example, the visual indicator may be a scoring or marking. Such visual indicators may beneficially provide builders with an indication of where such sensor assembles are located, and therefore which areas of a panel should be avoided for drilling, nailing, or otherwise penetrating the panel during installation. As mentioned herein, the sensors may be spaced at a consistent distance over the length of the panel, such as at 1 foot, 2 foot, 3 foot, or other spacings. Likewise, the visual indicators 121 may be similarly spaced. For example, the at least one environmental sensor assembly may include a plurality of environmental sensor assemblies spaced from one another at a distance of from about 1 foot to about 4 feet.

Methods

Methods of manufacturing construction panels and materials described herein are also provided. For example, a gypsum panel, fiber-reinforced gypsum panel, isocyanurate panel, polymeric rain screen, polymeric sound mitigation mat, polymeric roofing drainage mat, wood-based panel, a flooring underlayment, or other construction material may be manufactured through any suitable means known in these industries. For example, as described above, the environmental sensor assembly may be associated with the panel, material, or underlayment during or after the manufacturing process. For example, the environmental sensor assembly may be embedded within a material forming of the panel or other material, or may be disposed between various layers (e.g., layers forming a panel core, facer, and/or coating) of the panel or material.

For example, in a gypsum panel, the environmental sensor assembly may be associated with the panel prior to or after setting of the gypsum core. In certain embodiments, the environmental sensor assembly is positioned in the gypsum slurry, for example at, near, or distal from the facer material, prior to setting. For example, the sensor assembly may be positioned within or on a surface of the panel core slurry during manufacturing, or may be positioned between layers of the panel core (e.g., between slurry layers, such as between the field and slate coat gypsum slurry layers).

In other embodiments, the environmental sensor assembly is attached or affixed to an external surface or edge of the gypsum panel. In other embodiments, the environmental sensor assembly is attached or affixed to a surface of the facer material opposite the gypsum core and covered by, embedded in, or surrounded by a coating material. In other embodiments, the environmental sensor assembly is attached or affixed between the facer material and the gypsum core.

In some embodiments, a plurality of sensor assemblies are disposed along a length of material (e.g., a paper backing, other membrane, fiberglass or other nonwoven scrim) in the desired spacing pattern and wound on a roll. During manufacturing, the roll of sensor assemblies may be unwound (such as by a spoiler) at the desired placement during manufacturing (e.g., between the slate coat and field (other gypsum) slurries or between the gypsum core and the facing material). In other embodiments, the sensor assemblies may be pre-applied to the inner face (e.g., panel core-facing) of the facing material. In another embodiment, the integrated circuit and/or antennae of the sensor assembly may be integrated within a fibrous mat facing material to increase the size of the antennae and read range.

Alternatively, as discussed above with reference to FIGS. 13 and 14, a poured-in-place gypsum or concrete panel system may be used for roofing or flooring underlayment applications, wherein the environmental sensor assembly is applied during the pour-in-place process.

In some embodiments, the environmental sensor assembly is applied in-line with the panel manufacturing process. In other embodiments, the environmental sensor assembly is applied post-panel manufacturing, such as at a construction site or intermediate storage or other manufacturing/processing facility.

Methods of making gypsum panels having water-resistive properties are also provided. In certain embodiments, during manufacturing, a gypsum slurry may be deposited on the uncoated surface of the facer material and set to form a gypsum core of the panel. Where the facer material is a fibrous mat, the gypsum slurry may penetrate some remaining fibrous portion of the thickness of the mat (i.e., some portion of the mat that is not already penetrated by the coating) and provide a mechanical bond for the panel. The gypsum slurry may be provided in one or more layers, having the same or different compositions, including one or more slate coat layers. As used herein, the term "slate coat" refers to a gypsum slurry having a higher wet density than the remainder of the gypsum slurry that forms the gypsum core. These methods may be used to produce gypsum panels having any of the features, or combinations of features, described herein. Enhanced penetration of the gypsum into the fibrous mat may be achieved by chemical modification of the gypsum slurry, by application of a penetration-enhancing coating on the surface of the fibrous mat contacted by the gypsum slurry, and/or by mechanical means.

In certain embodiments, the external surface of the fibrous mat is coated with a continuous barrier coating that penetrates a portion of the first fiberglass mat, to define the remaining portion of the first fiberglass mat that gypsum crystals of the gypsum core penetrate, such that voids in the first fiberglass mat are substantially eliminated.

In certain embodiments, the gypsum core includes multiple layers that are sequentially applied to the fiberglass mat, and allowed to set either sequentially or simultaneously. In other embodiments, the gypsum core includes a single layer. In some embodiments, a second fiberglass mat may be deposited onto a surface of the final gypsum slurry layer (or the sole gypsum slurry layer), to form a dual mat-faced gypsum panel. For example, the first and/or second fiberglass mat may include a barrier coating on its surface that penetrates a portion of the mat. The gypsum slurry or multiple layers thereof may be deposited on the fiberglass mat by any suitable means, such as roll coating.

In some embodiments, the gypsum core includes at least three gypsum layers, with the outermost gypsum layers of the gypsum core (i.e., the layers that form an interface with the fiberglass mats). In certain embodiments, both outermost layers are chemically altered for enhanced penetration.

In certain embodiments, the first and/or second fibrous mats are already coated upon contacting the gypsum (or other panel core) slurry. In some embodiments, the methods include applying the continuous coating to the first and/or second fibrous mat, either before or after contacting the mats with the panel core slurry. In certain embodiments, applying the barrier coating includes spray coating, ribbon coating, curtain coating, knife coating, or direct roll coating. In some embodiments, the barrier coating is applied to each of the first and/or second fibrous mats in an amount from about 1 pound to about 9 pounds, per 100 ft$^2$. For example, the barrier coating may be applied to the first and/or second fibrous mat in an amount from about 2 pounds to about 8 pounds, per 100 ft$^2$. In other embodiments, coated fibrous mats may be obtained in a pre-fabricated form.

In some embodiments, the method also includes mechanically vibrating at least the first fiberglass mat having the first gypsum slurry deposited thereon to effect penetration of the gypsum slurry into the remaining fibrous portion of the first fiberglass mat.

In certain embodiments, the panel core slurry (or layers thereof) may be deposited on the non-coated side of a horizontally oriented moving web of pre-coated fibrous mat. A second coated or uncoated fibrous mat may be deposited onto the surface of the panel core slurry opposite the first coated fibrous mat, e.g., a non-coated surface of the second coated fibrous mat contacts the panel core slurry. In some embodiments, a moving web of a pre-coated or uncoated nonwoven fibrous mat may be placed on the upper free surface of the aqueous panel core slurry. Thus, the panel core material may be sandwiched between two fibrous mats, one or both having a barrier coating. In certain embodiments, allowing the panel core material and/or continuous barrier coating to set includes curing, drying, such as in an oven or by another suitable drying mechanism, or allowing the material(s) to set at room temperature (i.e., to self-harden).

In certain embodiments, as shown in FIGS. 1 to 9, dry ingredients (not shown) from which the gypsum core is formed are pre-mixed and then fed to a mixer of the type commonly referred to as a pin mixer 2. Water and other liquid constituents (not shown) used in making the core are metered into the pin mixer 2 where they are combined with the dry ingredients to form an aqueous gypsum slurry. The slurry 4 is dispersed through one or more outlets at the bottom of the mixer 2 onto a moving sheet of fibrous mat 6. The sheet of fibrous mat 6 is indefinite in length and is fed from a roll (not shown) of the mat. In certain embodiments, the two opposite edge portions of the fibrous mat 6 are progressively flexed upwardly from the mean plane of the mat 6 and then turned inwardly at the margins so as to provide coverings for the edges of the resulting board 40. In FIG. 1, this progressive flexing and shaping of the edges of the mat 6 are shown for only one side edge of the mat and the conventional guiding devices which are ordinarily employed for this purpose are omitted from the figure for the sake of clarity. FIG. 7 shows an edge of the set gypsum core 42 covered by the overlapped edge portion 6A of the mat 6. FIG. 7 shows also score marks 10 and 10A of the mat 6, the score marks permitting the formation of good edges and flat surfaces. The score marks 10 and 10A are made by a conventional scoring wheel 12. An advantage of using the glass fiber mat is that it is capable of being scored and edged like conventional paper facing.

Another sheet of fibrous mat 16 is fed from a roll (not shown) onto the top of slurry 4, thereby sandwiching the slurry between the two moving fibrous mats which form the slurry. The mats 6 and 16 with the slurry 4 sandwiched therebetween enter the nip between the upper and lower forming or shaping rolls 18 and 20, and are thereafter received on a conveyer belt 22. Conventional edge guiding devices, such as indicated at 24, shape and maintain the edges of the composite until the gypsum has set sufficiently to retain its shape. In due course, sequential lengths of the board are cut and further processed by exposure to heat which accelerates the drying of the board by increasing the rate of evaporation of excess water in the gypsum slurry.

With reference to FIG. 7, it has been observed that the set gypsum of the core 42 is effective in forming satisfactory bonds with the mats and between the edge portions of the overlying mat 16 and the overlapped edge portion 6A of the underlying mat 6, thus making it unnecessary to use a bond improver in the slurry or an edge paste to form the aforementioned bonds.

In certain embodiments, the method of making the panel includes associating a self-supporting environmental sensor assembly with the panel. For example, the environmental sensor assembly may be any suitable assembly described herein, such as those including an antenna, a processing module, and a wireless communication module, and configured to detect an environmental condition of the panel and wirelessly communicate data on the environmental condition to a reader.

In some embodiments, methods include associating a visual indicator of the location of the sensor assembly with the panel. For example, marking, scoring, or other methods of creating the indicator may be performed inline, assisted by metal detection of the sensor assemblies, or may be created at regular intervals corresponding to the regular intervals at which the sensor assemblies were known to have been spaced. In other embodiments, the indicators may be pre-printed on the facing material or other external surface of the panel, to correspond with a known pattern of the placement of the sensor assemblies.

Applications

Systems and methods for detecting an environmental condition at a panel or other construction material are also provided herein. In certain embodiments, a system includes at least one of the building panels, materials, or flooring underlayments described herein along with at least one reader for receiving the data wirelessly communicated from the environmental sensor assembly. In certain embodiments, a system includes at least one panel containing an environmental sensor assembly, such as are described herein, and at least one reader for receiving the data wirelessly communicated from the environmental sensor assembly. In certain embodiments, a method of monitoring an environmental condition of a panel includes providing at least one panel having an environmental sensor assembly associated therewith, detecting an environmental condition of the panel, via the environmental sensor assembly, and wirelessly communicating data on the environmental condition from the environmental sensor assembly to a reader.

The reader may be any suitable wireless sensor reader known in the art. For example, the reader may be a handheld manual reader. In other embodiments, the reader is a stationary powered reader mounted at a building containing the at least one panel, material, or underlayment. For example, a stationary powered reader may be located at or adjacent the panels, or may be located at some distance (e.g., 10 to 100 feet, such as 10 to 50 feet, such as 25 to 30 feet) from the panels. For example, at a building containing one or more panels having environmental sensor assemblies installed as roof deck, interior/exterior sheathing panels, mats, or other structural panels, a powered reader may be mounted at one or more sites on and/or around the building to continuously or intermittently monitor the status of the environmental sensor assemblies. In certain embodiments, a building control system is provided to receive information from the reader(s). In some embodiments, a reader may be mounted on a drone that is configured to approach the at least one panel to receive the data wirelessly communicated from the environmental sensor assembly. In certain embodiments, the sensing data is digitized and wirelessly communicated to off-the-shelf readers using a standard UHF Gen 2 protocol READ command for further processing.

In certain embodiments, the system also includes a processing unit and the reader is configured to communicate the data on the environmental condition to the processing unit, and the processing unit is operable to determine at least one condition status at the environmental sensor assembly from the data. For example, the reader may be configured to communicate the impedance value representative of the reactive component impedance to the processing unit, such that the processing unit is operable to determine at least one condition status at the environmental sensor assembly from the impedance value representative of the reactive component impedance.

In certain embodiments, the system includes an integration service that allows for programming of the sensors without requiring complex IT infrastructure and middleware. For example, the integration service may provide for a repository of all sensor tag-related data, e.g. sensor range and calibration data, that can be accessed securely by authorized web services and apps, a repository of measurement data related to the sensor-tagged panels, and a decision flow engine, e.g. so that if an sensor-tagged panel exceeds a preset level (e.g., a preset moisture level), a notification is sent by SMS/email to a service technician.

In certain embodiments, raw data is collected from these sensors via the reader for processing to be performed by a data processing unit where computation occurs to determine a humidity or temperature measurement. Further, with reference to FIG. 20, wireless communication engine 2104 and sensor engine 2106 may be fully programmable via wireless methods. Passive RFID sensors of FIG. 20 may be deployed as an array of smart sensors (e.g., multiple sensor assemblies on one or multiple panels installed at a single site) to collect data that may be sent back to a central processing unit. Another embodiment provides an environmental sensing method for use in an RF system including the steps of: calibrating an RF sensor by developing a first calibration value indicative of an absence of a detectable quantity of a substance and a second calibration value indicative of a presence of the detectable quantity of the substance, installing the sensor in a structure, exposing the structure to the substance, interrogating the sensor to retrieve a sensed value, and detecting the presence of the substance in the structure as a function of the sensed value relative to the first and second calibration values.

Figure 19:
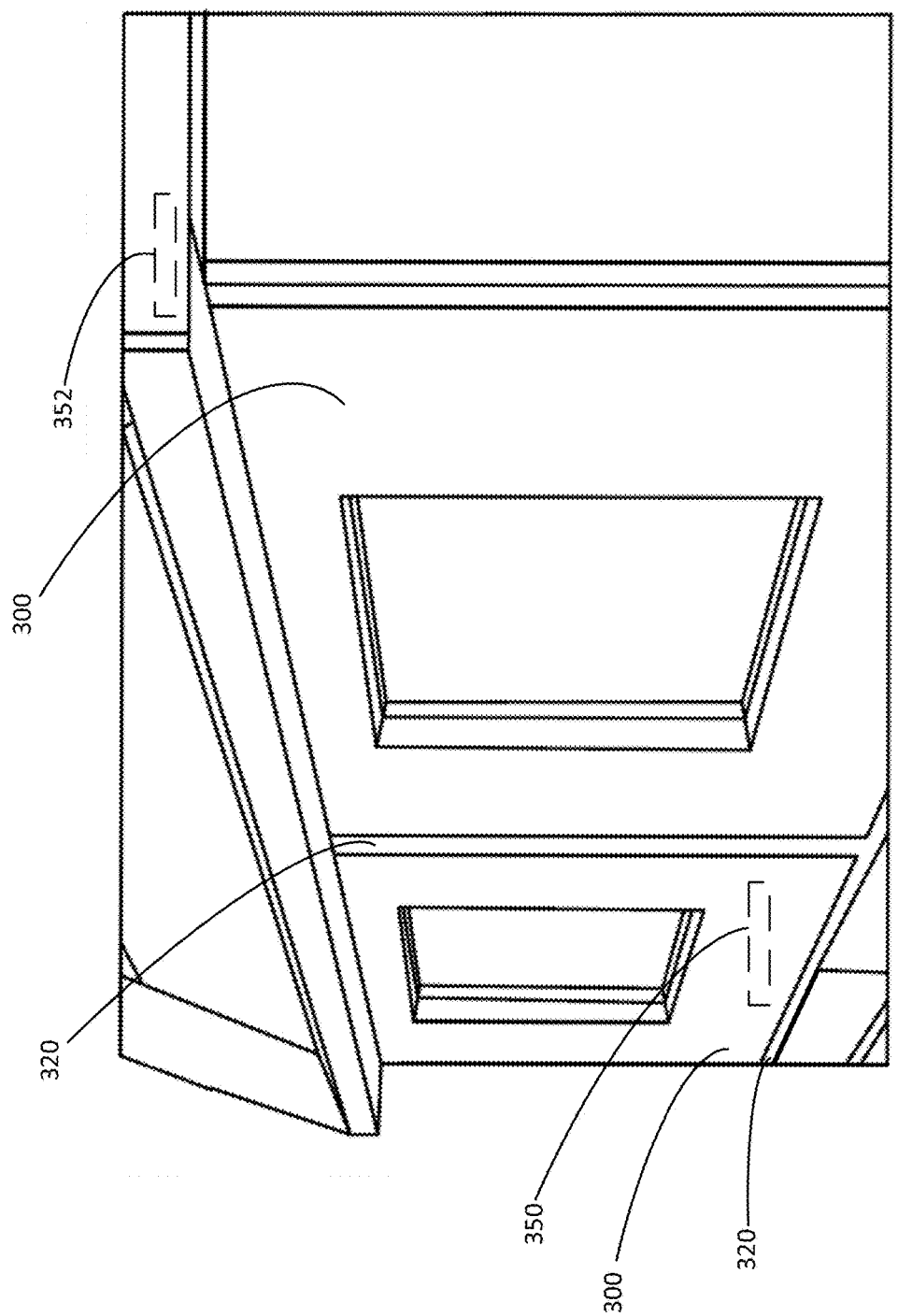
FIG. 19 is a perspective view of a building sheathing system having water-resistive and air-barrier properties.

As shown in FIG. 19, a building may include a sheathing system including at least two panels 300 and a seaming component 320 configured to provide a seam at an interface between at least two of the panels 300. Environmental sensor assemblies may be provided on or in one or more internal wallboard, external sheathing, or roof panels, as described herein, with the location of such assemblies indicated externally by visual indicators 350, 352. In particular, such panels having environmental sensor assemblies may be useful in sheathing or roofing systems in which improved water resistance is desired, so that water infiltration may be detected quickly and efficiently.

In certain embodiments, the seaming component in such systems includes tape or a bonding material. For example, the seaming component may be a tape including solvent acrylic adhesives, a tape having a polyethylene top layer with butyl rubber adhesive, a tape having an aluminum foil top layer with butyl rubber adhesive, a tape having an EPDM top layer with butyl rubber adhesive, a tape having a polyethylene top layer with rubberized asphalt adhesive, or a tape having an aluminum foil top layer with rubberized asphalt adhesive. For example, the seaming component may be a bonding material such as synthetic stucco plasters, cement plasters, synthetic acrylics, sand filled acrylics, solvent based acrylics, solvent based butyls, polysulfides, polyurethanes, silicones, silyl modified polymers, water-based latexes, EVA latexes, or acrylic latexes. Thus, the above-described panels may be installed with either a tape, liquid polymer, or other suitable material, to effectively treat areas of potential water and air intrusion, such as seams, door/window openings, penetrations, roof/wall interfaces, and wall/foundation interfaces. As such, the building sheathing panels, when used in combination with a suitable seaming component, may create an effective water-resistive and/or air-barrier envelope.

Thus, in certain embodiments, the building construction panels, materials, and underlayments described herein are configured to detect moisture, temperature, or pressure on roofs, on other exterior building components, on exterior building components covered with a membrane of other covering, within roofs or walls, and within the building envelope. The system is configured to detect environmental conditions that could lead to the deterioration of roof systems or other building components. Thus, the systems described herein may advantageously provide early detection of moisture intrusion prior to damaging the roof, flooring, walls, or other regions of the building system.

Instead of the traditional manual inspections of roofing and/or other panels, the use of the readers described herein will reduce or eliminate the labor associated with inspections. The readers could be handheld or could be attached to a drone which would transport a reader from tag to tag (i.e., sensor assembly to sensor assembly). Alternately, the reader would be a powered reader, such as those used in highway and DOT applications, mounted on a roof or other location that reads the tags and relays the information over the internet or similar system to a smart building control system. In addition to external sheathing and roofing applications, the panels and sensors could also be used in the interior of the building, to identify moisture intrusion anywhere in the building, including mold and mildew resistant basement applications, behind shower and tile board, and/or on or behind exterior sheathing.

In certain embodiments, methods and systems for detecting environmental conditions further include identification of a building panel or portion of a building panel at which the condition is detected, such as through the visual indicators discussed herein. The methods may further include repairing the building panel or portion of the panel identified as being damaged. For example, such systems and methods may enable a building owner to determine in real time when their roof, walls, flooring, etc. are damaged in a manner that may affect energy efficiency, water intrusion, or other performance characteristics. For example, a typical moisture intrusion issue may take up to a year or more to detect, which would likely require replacement of a significant amount of building panels. In contrast, the disclosed systems would identify a moisture intrusion issue as soon as one portion of a panel is affected. As such, these systems allow for remediation or replacement of only a section of a panel or a single panel. Similarly, temperature issues, which may result in a degradation of panel core materials, can also be detected in real time.

Moreover, the present panels eliminate the need for wired sensors and sensors containing a microcontroller, in which the labor involved in programming and installation is very high. In these wired embodiments, a technician having microcontroller/PLC programming knowledge would have to program the system to operate. The present system will be virtually plug-and-play, and any programming may be done before panel installation in the form of a GUI (graphical user interface) that will integrate with existing facility management software. In systems having a stationary reader(s), such as commercial buildings, the reader advantageously may by connected to the building network and maintained by a building engineer along with other facility systems (e.g., HVAC, fire suppression, lighting, occupancy control).

EXAMPLES

Building panels and representative samples having the described environmental sensor assemblies were manufactured and subjected to various performance tests.

First, sample building panels were prepared with environmental sensor assemblies located at various positions within the panel, including within or on a surface of the panel core (e.g., between the panel core and a facing material) and on an external surface of the panel. These panel samples were exposed to typical panel handling and installation conditions, as well as were coated with exemplary coating materials, such as solvent-based and water-based adhesives and hot asphalt. It was observed that the sensor assemblies located on the surface of the panels were much more susceptible to damage from handling. Additionally, the adhesives and asphalt were observed to cause damage to the sensor assemblies that prevented accurate readings of conditions such as temperature and moisture. In contrast, sensor assemblies located within or on a surface of the panel core (internal to the overall panel) did not suffer from these issues.

Next, these panels were tested to determine whether any difference in the accuracy of a panel moisture condition detection by the sensor assembly was present in sensor assemblies located within or on a surface of the panel core (i.e., within the panel) versus on the external surface of the board. Specifically, drops of water were placed directly on the sensor assembly disposed on the external surface of the panel and the percent free moisture reading of the panel was tested at both the external sensor and the internal panel sensor. Generally, the surface sensors read as a "very wet" condition, despite the moisture saturation of the panel itself not changing. Embedding the sensor assembly into the panel core correlated well with percent free moisture and laboratory moisture meters. That is, false high readings were obtained from localized surface wetting in sensor assemblies located on the external panel surface, whereas the embedded sensor assemblies more closely replicated the true moisture content of the panel.

Figure 27:
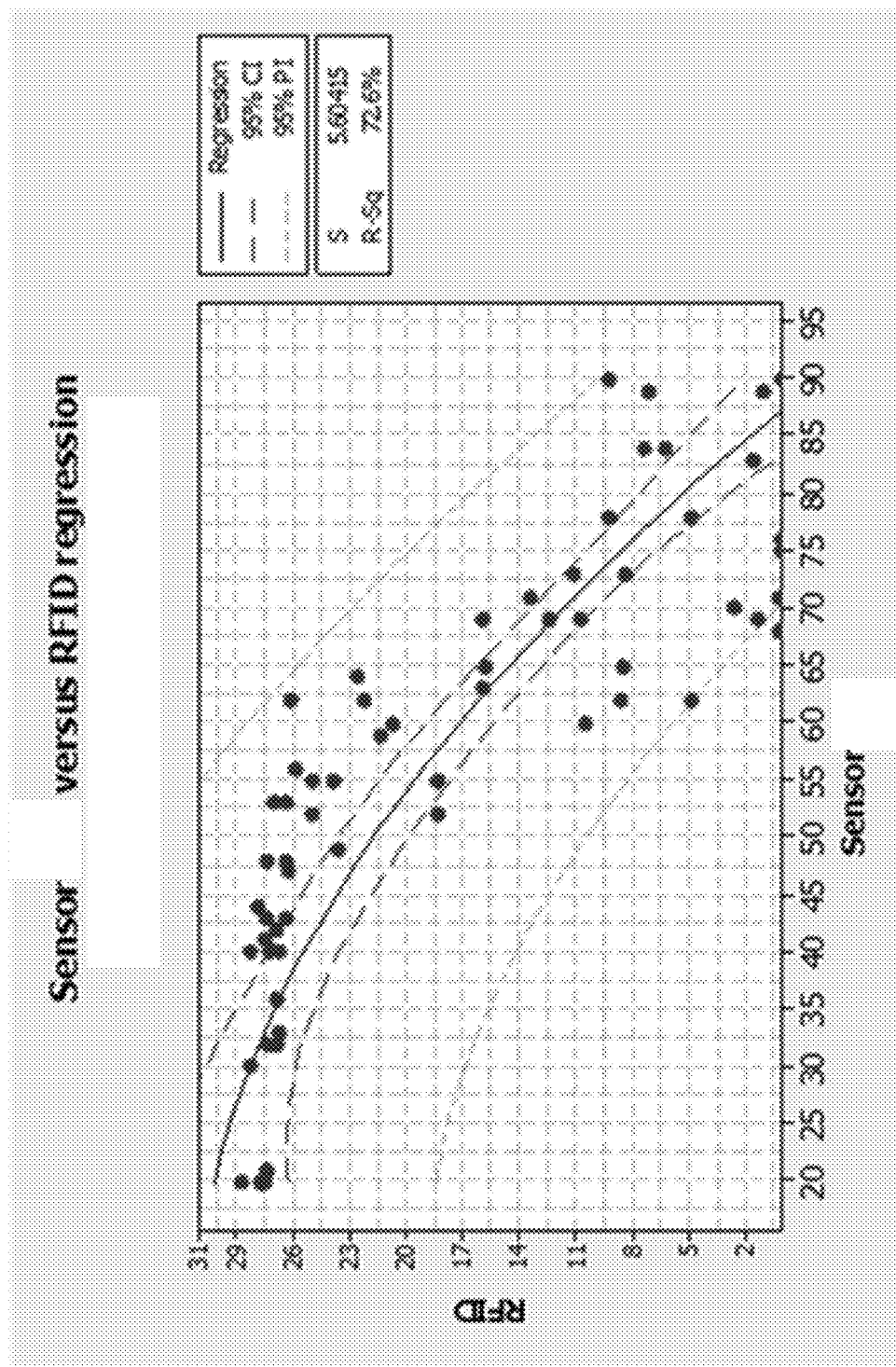
FIG. 27 is a graph showing a regression plot of the sensor versus RFID readings, as measured in the Examples.

Next, the sample panels having internally embedded RFID sensors were completely immersed in water for approximately 6 hours. Panel moisture content readings were taken every 5 minutes by both the internal sensor assembly and a laboratory moisture meter, to determine the relative accuracy of the embedded sensor assemblies. The results of this test are shown in FIG. 27, which is a regression plot of the laboratory sensor (labeled "sensor" in graph) versus the embedded RFID readings. The correlation coefficient ($R^2$) was 72.6%. As can be seen, the embedded RFIC sensor assemblies significantly trended with the lab moisture meter readings.

Figure 28:
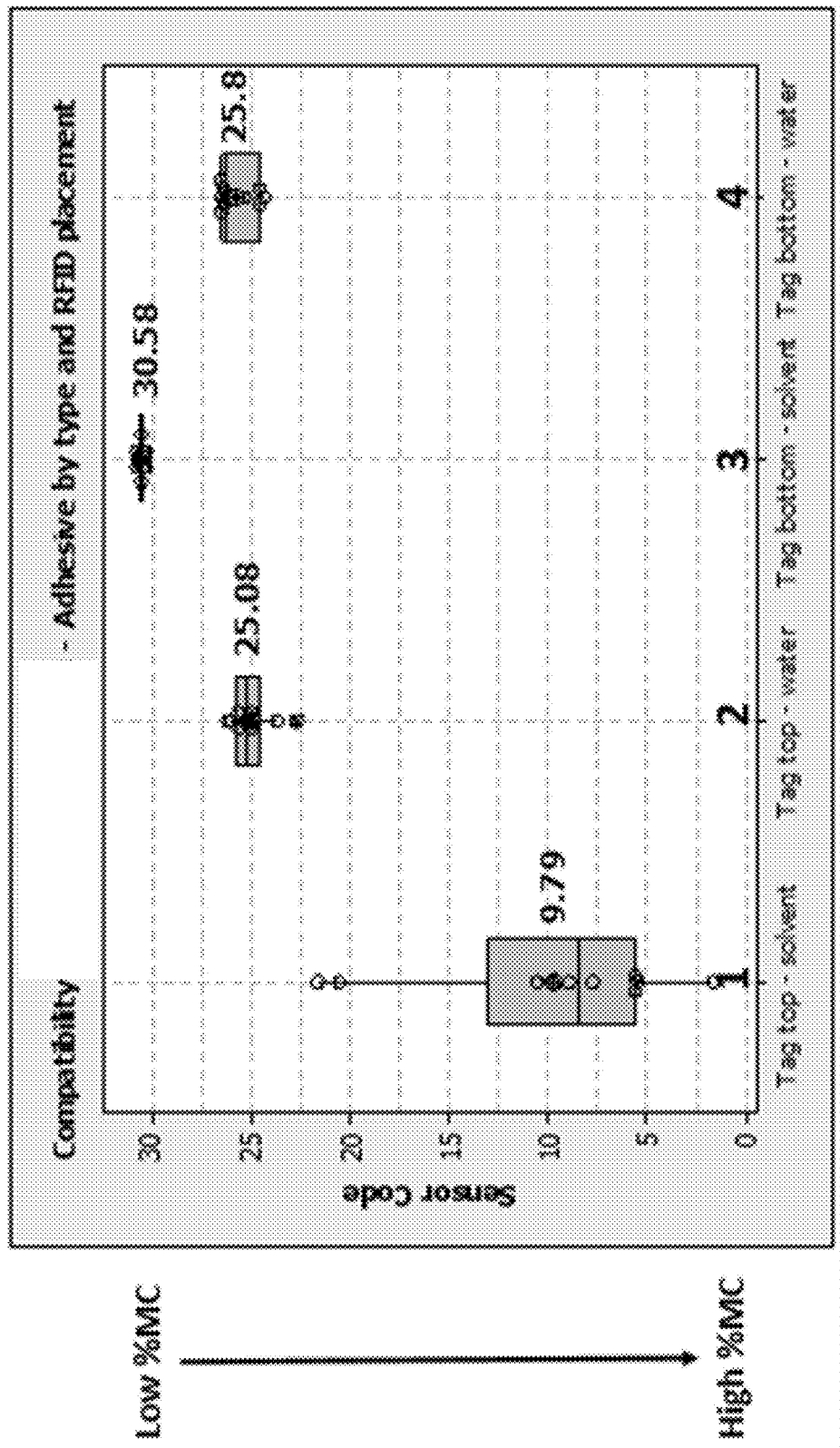
FIG. 28 is a graph showing the sensor codes of various combinations of adhesives and sensor placements in samples of the Examples.

Next, sample panels with four combinations of sensor assembly placement and panel surface adhesive exposure were tested. Condition 1 included a sensor assembly positioned on the external surface of the panel in direct contact with a solvent-based adhesive. Condition 2 included a sensor assembly positioned on the external surface of the panel in direct contact with a water-based adhesive. Condition 3 included a sensor assembly at the opposed surface of the sample panel (to represent a sensor assembly within the core or otherwise spaced from the external surface exposed to the adhesive) with the opposite surface exposed to the solvent-based adhesive. Condition 4 involved a sensor assembly at the opposed surface with the external surface exposed to the water-based adhesive. The moisture readings of the RFID sensor assemblies were taken after the adhesives were allowed to cure for one week. FIG. 28 is a graph showing the sensor codes detected in these samples. A sensor code of about 30 or above is "dry", with lower codes representing increasingly high moisture content. As can be seen, the sensor assemblies positioned in direct contact with the solvent-based adhesive displayed significant read variation, possibly due to interference by the chemistry of the adhesive. The sensor assembly representing the internally disposed sensor assembly and exposed to the solvent-based adhesive performed the best. Thus, building panels of the present disclosure that require an external membrane or other external coating or covering may utilize a solvent-based adhesive to apply such membrane, coating, or covering. The sensor assemblies exposed to the water-based adhesive performed better than the assembly in direct contact with the solvent-based adhesive, with the sensor assembly in direct contact with the water-based adhesive performing slightly worse than the "internal" sensor assembly.

Figure 25:
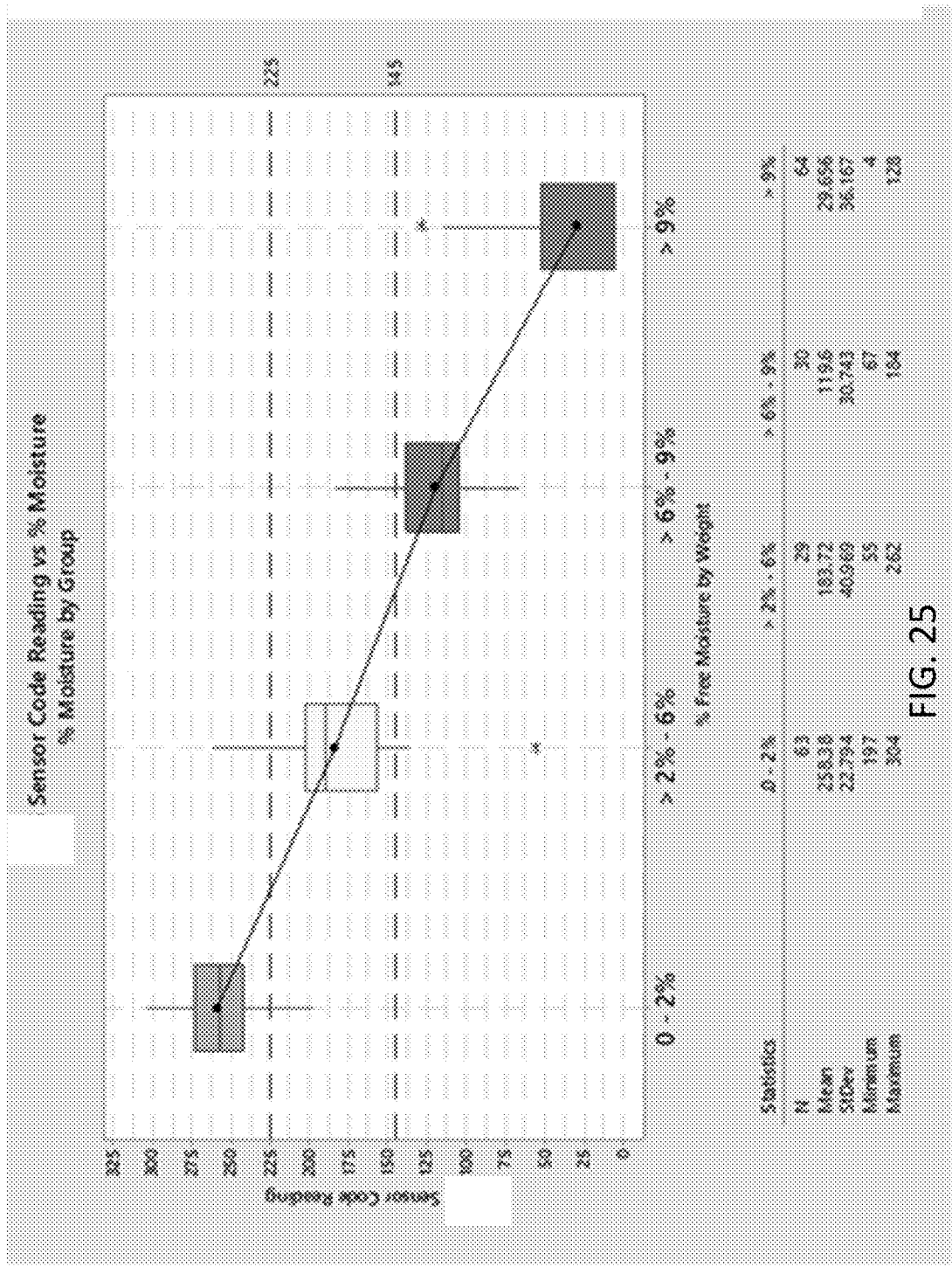
FIG. 25 is a graph showing the sensor code reading versus the percent free moisture, by weight, as measured in the Examples.
Figure 26:
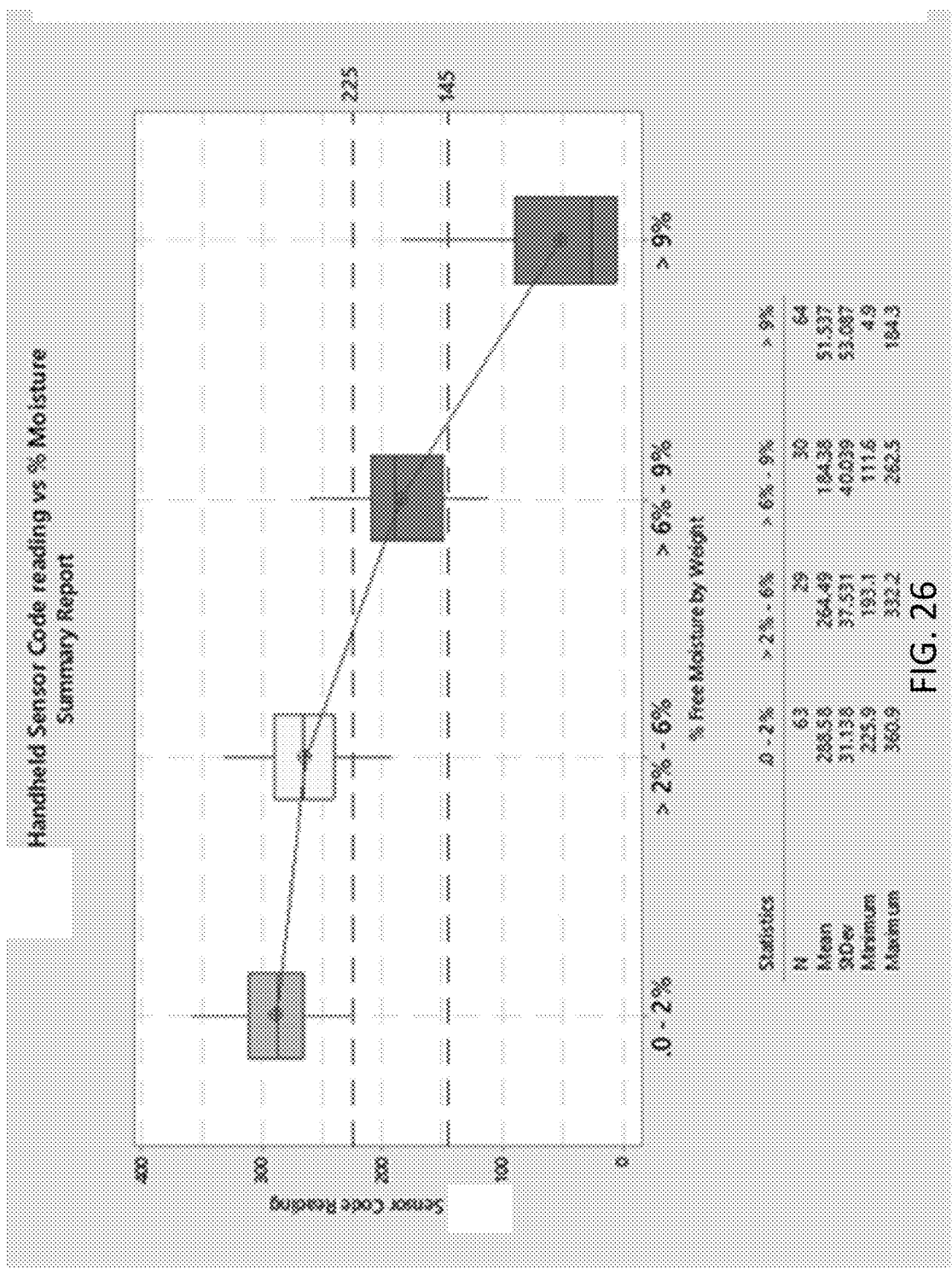
FIG. 26 is a graph showing the handheld sensor code reading versus the percent free moisture, by weight, as measured in the Examples.

Next, sample panels containing RFID sensor assemblies were tested for accuracy of the sensor readings (measured using a handheld reader and a fixed sensor reader) relative to a laboratory moisture meter reading. Specifically, 30 samples were heated in an oven to remove all free moisture. The samples were then removed from the oven and their dry weight was documented. RFID sensor code readings for moisture content were taken using the NORDIC ID Merlin 1 handheld 1 watt RFID tag reader and the FEIG ELECTRONICS fixed tag reader (Reader ID MAX.U1002-FCC and Antenna ID ISC.ANT.U600/270-FCC Antenna UHF). Moisture readings were also taken using a laboratory moisture meter and documented for comparison. The samples were submerged in water for 5 hours then removed. The samples were patted dry using paper towels. The samples were re-weighed, and sensor codes were read and documented using the Nordic and FEIG systems along with moisture meter readings. Submersion, pat drying, and code readings were repeated at 24, 48, and 120-hour intervals. FIG. 25 is a graph showing the fixed reader code reading versus the percent free moisture (as measured by the moisture meter), by weight. FIG. 26 is a graph showing the handheld reader code reading versus the percent free moisture (as measured by the moisture meter), by weight. Generally, a free moisture content of 0-2% was considered a dry panel, a free moisture content of 2-6% was considered a damp panel, and a free moisture content of 6% or more was considered a wet panel. As can be seen in the results, the fixed reader gave results more consistent with the laboratory meter, on average indicating the correct moisture condition at each level (dry, damp, wet).

Thus, it has been demonstrated that environmental sensor assemblies may be associated with a building panel (e.g., embedded in or associated with a panel core) to provide useful readings on environmental conditions, such as moisture, at the panel. Sensor assemblies provided within the core were discovered to display improved performance and accuracy.

While the disclosure has been described with reference to a number of embodiments, it will be understood by those skilled in the art that the invention is not limited to such disclosed embodiments. Rather, the invention can be modified to incorporate any number of variations, alterations, substitutions, or equivalent arrangements not described herein, but which are commensurate with the spirit and scope of the invention. Additionally, while various embodiments of the invention have been described, it is to be understood that aspects of the invention may include only some of the described embodiments. Accordingly, the invention is not to be seen as limited by the foregoing description, but is only limited by the scope of the appended claims.

What is claimed is:

1. A building panel, comprising:
   a panel comprising a panel core and having a first surface and an opposed second surface; and
   at least one environmental sensor assembly associated with the panel core and configured to detect an environmental condition of the panel comprising moisture, pressure, or both, and wirelessly communicate data on the environmental condition to a reader, wherein the at least one environmental sensor assembly is self-supporting, passive, and comprises an antenna, a processing module, and a wireless communication module, and wherein the at least one environmental sensor assembly is disposed between layers forming the panel core, or disposed between the first surface of the panel core and a panel facing material.

2. The building panel of claim 1, wherein the panel core comprises a gypsum panel core.

3. The building panel of claim 2, wherein:
the gypsum panel core comprises a first gypsum layer and a second gypsum layer, the first gypsum layer comprising a slate coat layer, and
the at least one environmental sensor assembly is disposed between the first and second gypsum layers.

4. The building panel of claim 3, wherein the first gypsum layer is present in an amount from about 2 percent to about 20 percent, by weight, of the gypsum panel core.

5. The building panel of claim 2, wherein:
the panel further comprises the panel facing material, which comprises a fiberglass facing mat, and
the at least one environmental sensor assembly is disposed between the first surface of the panel core and the fiberglass facing mat.

6. The panel of claim 1, wherein the at least one environmental sensor assembly comprises a passive radio frequency identification sensor.

7. A system for detecting an environmental condition at a panel, comprising:
at least one of the building panels of claim 1; and
at least one reader for receiving the data wirelessly communicated from the at least one environmental sensor assembly.

8. The system of claim 7, further comprising a processing unit, wherein the reader is configured to communicate the data on the environmental condition to the processing unit, and the processing unit is operable to determine at least one condition status at the at least one environmental sensor assembly from the data.

9. The system of claim 7, wherein the at least one reader comprises a stationary powered reader positioned at or near the least one building panel or a handheld manual reader.

10. A method of detecting an environmental condition, comprising:
providing at least one of the building panels of claim 1; and
wirelessly communicating data on the environmental condition from the at least one environmental sensor assembly to a reader.

11. The method of claim 10, further comprising:
communicating the data on the environmental condition to a processing unit; and
determining, at the processing unit, at least one condition status at the at least one environmental sensor assembly.

12. The method of claim 10, wherein the environmental condition comprises moisture.

13. A method, comprising:
the method of claim 12; and
repairing the building panel or a portion of the building panel at which a moisture condition is detected.

14. The method of claim 13, further comprising identifying the portion of the building panel at which the moisture condition is detected by locating at least one visual indicator positioned on an external surface of the panel, each of the at least one visual indicators indicating a location of an environmental sensor assembly within the building panel.

15. The method of claim 14, wherein the at least one visual indicator comprises a score or mark.

16. A building panel, comprising:
a panel comprising a panel core and having a first surface and an opposed second surface; and
at least one environmental sensor assembly associated with the panel core and configured to detect an environmental condition of the panel comprising moisture, pressure, or both, and wirelessly communicate data on the environmental condition to a reader,
wherein the at least one environmental sensor assembly is self-supporting, passive, and comprises an antenna, a processing module, and a wireless communication module, and wherein:
the panel comprises a first external surface and an opposed second external surface, and
the building panel further comprises at least one visual indicator positioned on the first external surface of the panel, each of the at least one visual indicators indicating a location of each of the at least one environmental sensor assemblies.

17. The building panel of claim 16, wherein the at least one visual indicator comprises a score or mark.

18. A building panel, comprising:
a panel comprising a panel core and having a first surface and an opposed second surface; and
at least one environmental sensor assembly associated with the panel core and configured to detect an environmental condition of the panel comprising moisture, pressure, or both, and wirelessly communicate data on the environmental condition to a reader,
wherein the at least one environmental sensor assembly is self-supporting, passive, and comprises an antenna, a processing module, and a wireless communication module, and
wherein the at least one environmental sensor assembly comprises a plurality of environmental sensor assemblies spaced from one another at a distance of from about 1 foot to about 4 feet.

19. A method of manufacturing a building panel, comprising:
combining a panel core slurry and a panel facing material to form a panel core having a first surface and an opposed second surface, the first surface being associated with the panel facing material; and
disposing at least one environmental sensor assembly within the panel core slurry or between the panel core slurry and the panel facing material, such that the at least one environmental sensor assembly is disposed between layers forming the panel core, or disposed between the first surface of the panel core and the panel facing material,
wherein the at least one environmental sensor is configured to detect an environmental condition of the panel comprising moisture, pressure, or both, and wirelessly communicate data on the environmental condition to a reader,
wherein the at least one environmental sensor assembly is self-supporting, passive, and comprises an antenna, a processing module, and a wireless communication module.

* * * * *